United States Patent
Macielag et al.

(10) Patent No.: US 7,776,855 B2
(45) Date of Patent: Aug. 17, 2010

(54) ANTIMICROBIAL OXAZOLIDINONE PRODRUGS

(75) Inventors: Mark J. Macielag, Branchburg, NJ (US); Manomi A. Tennakoon, Hillsborough, NJ (US)

(73) Assignee: Janssen Pharmaceutica N.V., Beerse (BG)

( * ) Notice: Subject to any disclaimer, the term of this patent is extended or adjusted under 35 U.S.C. 154(b) by 462 days.

(21) Appl. No.: 11/774,746

(22) Filed: Jul. 9, 2007

(65) Prior Publication Data

US 2008/0027053 A1 Jan. 31, 2008

Related U.S. Application Data

(60) Provisional application No. 60/820,497, filed on Jul. 27, 2006, provisional application No. 60/848,659, filed on Oct. 2, 2006.

(51) Int. Cl.
*A61K 31/42* (2006.01)
*A61K 31/497* (2006.01)
*C07D 263/04* (2006.01)
*C07D 403/00* (2006.01)
*C07D 413/14* (2006.01)

(52) U.S. Cl. .............. 514/234.2; 514/254.02; 514/376; 544/137; 544/370; 548/229

(58) Field of Classification Search ............... None
See application file for complete search history.

(56) References Cited

U.S. PATENT DOCUMENTS 6,413,981 B1  7/2002  Paget et al.

FOREIGN PATENT DOCUMENTS

| WO | WO 99/52903 | 10/1999 |
|---|---|---|
| WO | WO 01/27106 | 4/2001 |
| WO | WO 2005/028473 | 3/2005 |

OTHER PUBLICATIONS

Zhu, Z.; Chen, H.; Goel, O. P.; Chan, O.H.; Stilgenbauer, L. A.; Stewart, B. H. *Bioorg Med. Chem. Lett.* 2000, 10, 1121.
Gray, M. D. M.; Smith, D. J. H. *Tetrahedron. Lett.* 1980, 21, 859.

*Primary Examiner*—Kamal A Saeed

(57) ABSTRACT

This invention includes oxazolidinone prodrug compounds of Formula (I) and Formula (II) as defined herein. The prodrugs are convertible by natural biological processes into an active ingredient possessed of antimicrobial properties useful in treating bacterial infections in mammals.

8 Claims, No Drawings

ANTIMICROBIAL OXAZOLIDINONE PRODRUGS

CROSS REFERENCE TO RELATED APPLICATIONS

This present application claims benefit of U.S. Provisional Patent Application Ser. No. 60/820,497, filed Jul. 27, 2006 and U.S. Provisional Patent Application Ser. No. 60/848,659, filed Oct. 2, 2006, which are incorporated herein by reference in their entirety and for all purposes.

FIELD OF THE INVENTION

This invention relates to compounds that are prodrugs of antimicrobial oxazolidinones. The invention also relates to pharmaceutical formulations of the compounds, and to methods of using the compounds to treat patients afflicted with various bacterial infections.

BACKGROUND OF THE INVENTION

Oxazolidinones are identified as a class of synthetic antimicrobial compounds, and possess activity against a variety of pathogens. Because of the increasing development of bacterial resistance to many antibiotics, oxazolidinones will play an important role in the treatment of infections.

Issues common to many oxazolidinones have been low absorption rate and poor water solubility. The development and administration of prodrugs can at times improve the pharmacological properties of oxazolidinones, as well as other drugs. Development of prodrugs is also often geared to enhancing water solubility, which simplifies the development of pharmaceutical formulations intended for intravenous administration. International Publication Number WO 2005/028473, published Mar. 31, 2005, identifies some possible prodrugs for certain oxazolidinones, namely acyloxymethylcarbamate derivatives according to the Formula (A) disclosed in the above publication:

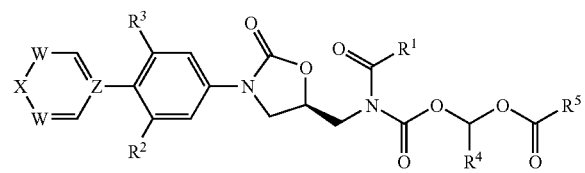

(A)

The variable moieties in Formula (A) are as described in the specification of the above-referenced published application. Forty-two specific compounds were identified as compounds that were synthesized and that fall within the limits of Formula (A).

SUMMARY OF THE INVENTION

The invention relates to oxazolidinone prodrug compounds having the Formula (I):

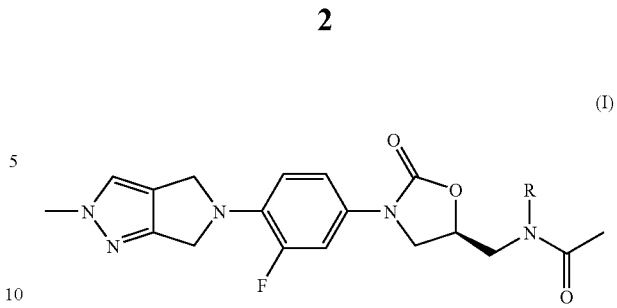

(I)

wherein R is a leaving group that undergoes a reaction in a biological matrix to produce the active ingredient of the structure of Compound 1:

Compound 1

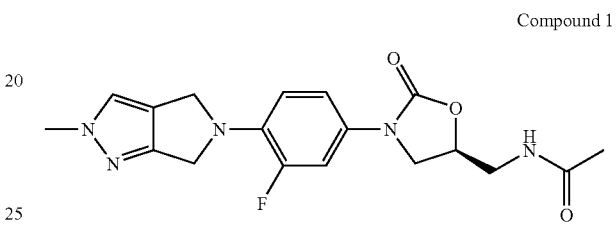

Compound 1 is described in detail in U.S. Pat. No. 6,413,981, which is incorporated herein by reference.

The invention also relates to oxazolidinone prodrugs of Formula (II):

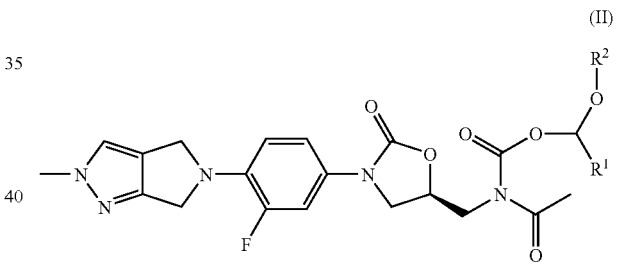

(II)

wherein:
$R^1$ is hydrogen or lower alkyl;
$R^2$ is selected from the group consisting of

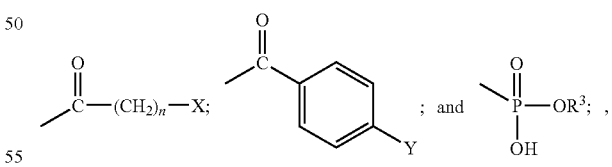

wherein, n is 0, 1, 2, 3 or 4;
X is selected from the group consisting of amino optionally substituted by one or two lower alkyl; heterocyclyl optionally substituted by one or more lower alkyl; and —O—$PO_3H_2$ or an alkyl ester thereof,
Y is selected from the group consisting of —$CH_2$O—$PO_3H_2$ or an alkyl ester thereof, and —O—$PO_3H_2$ or an alkyl ester thereof,
$R^3$ is hydrogen or lower alkyl; or a pharmaceutically acceptable salt thereof.

This invention also relates to pharmaceutical formulations including an oxazolidinone prodrug of Formula (I) or (II) as active pharmaceutical ingredient, and one or more pharmaceutically acceptable excipients, diluents, fillers, or the like to form a solid or liquid dosage form adapted for administration by oral or parenteral routes to warm-blooded mammals, including humans.

The invention also relates to methods for treating patients suffering from microbial diseases by administering an effective amount of a compound of Formula (I) or (II) or a pharmaceutical formulation comprising a Formula (I) or (II) compound and one or more pharmaceutically acceptable excipients, diluents, fillers, or the like.

DETAILED DESCRIPTION OF THE INVENTION

In embodiments of the present invention, the oxazolidinone prodrugs of Formula (II) include compounds wherein:
$R^1$ is hydrogen or lower alkyl;
$R^2$ is selected from the group consisting of

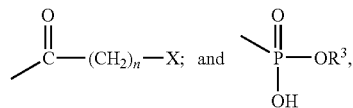

wherein n is 1;
X is selected from the group consisting of amino optionally substituted by one or two lower alkyl; and, heterocyclyl, optionally substituted by one or more lower alkyl;
$R^3$ is lower alkyl; or a pharmaceutically acceptable salt thereof.

In an embodiment of the present invention, the oxazolidinone prodrugs of Formula (II) include compounds wherein:
$R^1$ is hydrogen or methyl;
$R^2$ is selected from the group consisting of

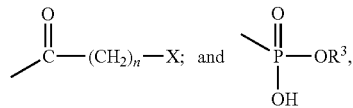

wherein n is 1;
X is selected from the group consisting of amino optionally substituted by one or two methyl; and, pyrrolidinyl, piperazinyl or morpholinyl, optionally substituted on pyrrolidinyl or piperazinyl by one methyl;
$R^3$ is ethyl; or a pharmaceutically acceptable salt thereof.

In an embodiment of the present invention, the oxazolidinone prodrugs of Formula (II) include compounds wherein X is selected from the group consisting of amino optionally substituted by one or two methyl; and, piperazinyl optionally substituted by one methyl.

DEFINITIONS

As used herein, these terms of art have the following meaning:

"Lower alkyl" means a fully saturated straight chain or branched chain hydrocarbon containing from one to no more than eight total carbon atoms. Examples of lower alkyl groups include methyl, ethyl, propyl, isopropyl, butyl, t-butyl, and others.

"Heterocyclyl" means a cyclic moiety of one or more rings, fused or unfused, wherein at least one ring atom is a non-carbon atom. Preferred heteroatoms include oxygen, nitrogen, sulfur and phosphorus, or any combination of two or more of those atoms. Examples of heterocyclic groups include pyrrolidinyl, piperidinyl, piperazinyl, morpholinyl, and others.

"Optionally substituted by" means the substitution of the listed groups for one or more hydrogen atoms thereof.

"Prodrug" means a precursor to a pharmaceutically active drug, which is converted into the active drug in the body by normal metabolic processes.

"Pharmaceutically acceptable salt" means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, triethanolamine, tromethamine, N-methylglucamine, and the like.

Compounds of this invention according to Formula (I) or Formula (II) are useful as prodrugs of the active ingredient (Compound 1) disclosed above.

In an embodiment of the present invention, the oxazolidinone prodrugs of Formula (II) include compounds selected from the group consisting of:

| Cpd | Name |
|---|---|
| 4a | Piperazin-1-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 4b | Piperazin-1-yl-acetic acid 1-(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-ethyl ester, |

-continued

| Cpd | Name |
|---|---|
| 5 | Dimethylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 6 | Morpholin-4-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 7 | 1-Methyl-pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 8 | (4-Methyl-piperazin-1-yl)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 9 | (tert-Butoxycarbonyl-methyl-amino)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 10 | Methylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 11 | (S)-Pyrrolidine-1,2-dicarboxylic acid 2-[(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl]ester 1-tert-butyl ester, |
| 12 | (S)-Pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 13 | 4-(Bis-benzyloxy-phosphoryloxymethyl)-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 14 | 4-Phosphonooxymethyl-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 15 | 4-(Bis-benzyloxy-phosphoryloxy)-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 16 | 4-Phosphonooxy-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 17a | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid di-tert-butoxy-phosphoryloxymethyl ester, |
| 17b | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(di-tert-butoxy-phosphoryloxy)-ethyl ester, |
| 18a | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid phosphonooxymethyl ester, |
| 18b | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-phosphonooxy-ethyl ester, |
| 20a | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid benzyloxy-ethoxy-phosphoryloxymethyl ester, |
| 20b | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(benzyloxy-ethoxy-phosphoryloxy)-ethyl ester, |
| 21a | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid ethoxy-hydroxy-phosphoryloxymethyl ester, |
| 21b | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(ethoxy-hydroxy-phosphoryloxy)-ethyl ester, |
| 23 | (Di-tert-butoxy-phosphoryloxy)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, and |
| 24 | Phosphonooxy-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester. |

In an embodiment of the present invention, the oxazolidinone prodrugs of Formula (II) include compounds selected from the group consisting of:

| Cpd | Name |
|---|---|
| 4a | Piperazin-1-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 4b | Piperazin-1-yl-acetic acid 1-(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-ethyl ester, |
| 5 | Dimethylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 6 | Morpholin-4-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 7 | 1-Methyl-pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 8 | (4-Methyl-piperazin-1-yl)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 10 | Methylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 12 | (S)-Pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 14 | 4-Phosphonooxymethyl-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 16 | 4-Phosphonooxy-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 18a | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid phosphonooxymethyl ester, |
| 18b | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-phosphonooxy-ethyl ester, |
| 21a | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid ethoxy-hydroxy-phosphoryloxymethyl ester, |
| 21b | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(ethoxy-hydroxy-phosphoryloxy)-ethyl ester, and |
| 24 | Phosphonooxy-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester. |

In an embodiment of the present invention, the oxazolidinone prodrugs of Formula (II) include compounds selected from the group consisting of:

| Cpd | Name |
|---|---|
| 4a | Piperazin-1-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 4b | Piperazin-1-yl-acetic acid 1-(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-ethyl ester, |
| 5 | Dimethylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |
| 8 | (4-Methyl-piperazin-1-yl)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, |

-continued

| Cpd | Name |
|---|---|
| 10 | Methylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, and |
| 21a | Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid ethoxy-hydroxy-phosphoryloxymethyl ester. |

Compound 1 is possessed of antimicrobial properties as described in U.S. Pat. No. 6,413,981, which is incorporated herein by reference.

With reference to U.S. Pat. No. 6,413,981, compounds of this invention include the following:

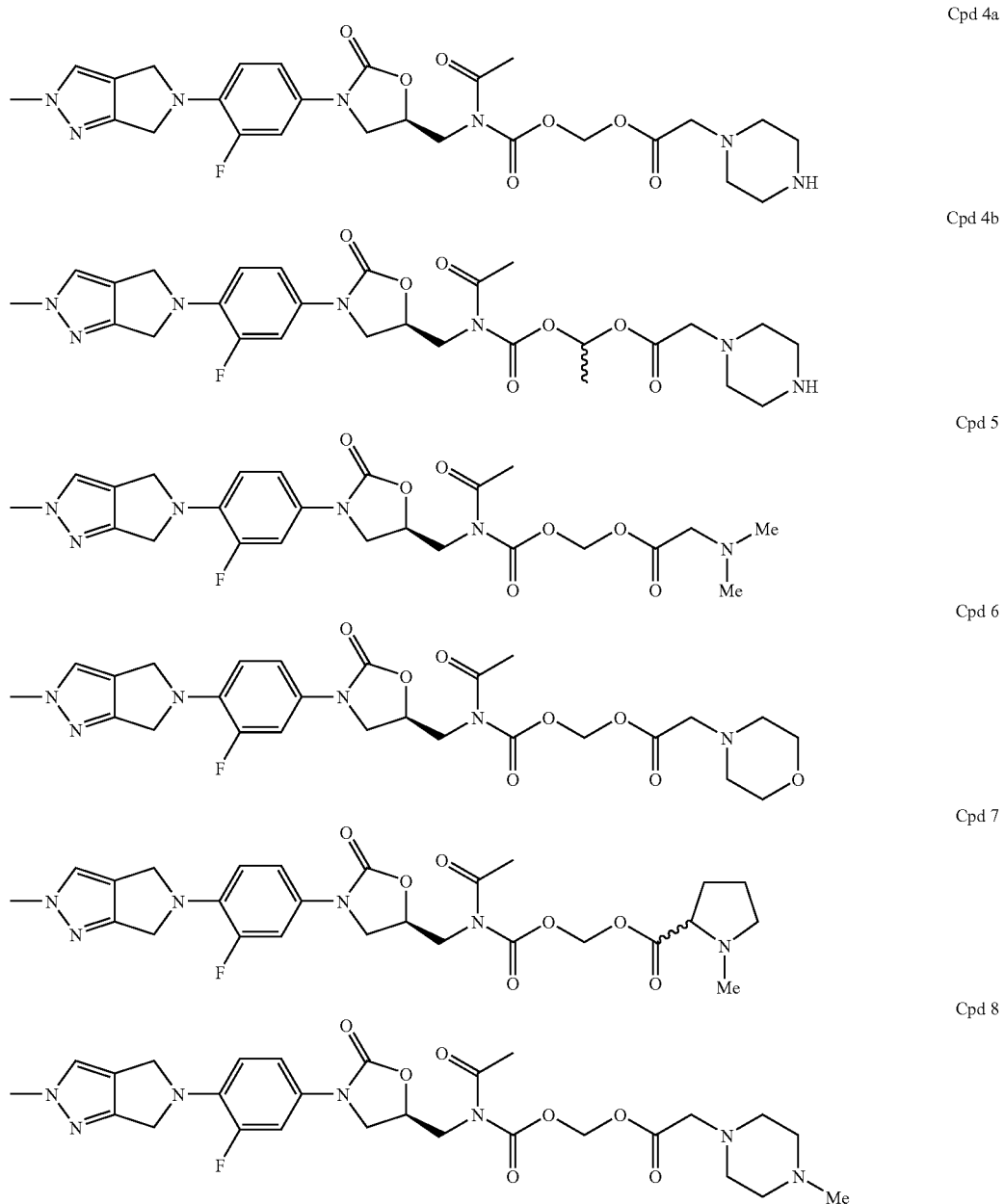

-continued
Cpd 10
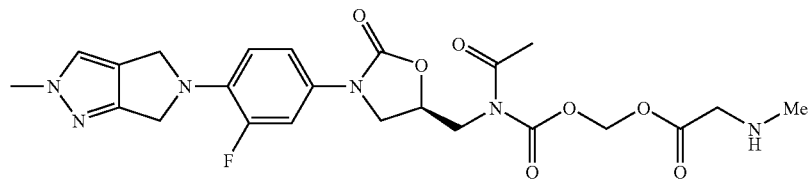
Cpd 12
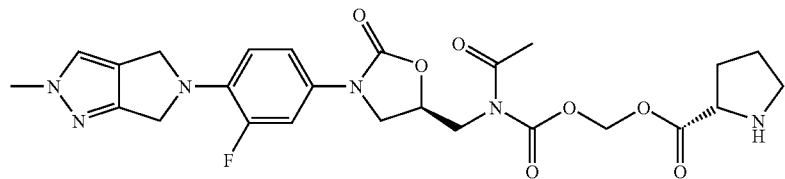
Cpd 14
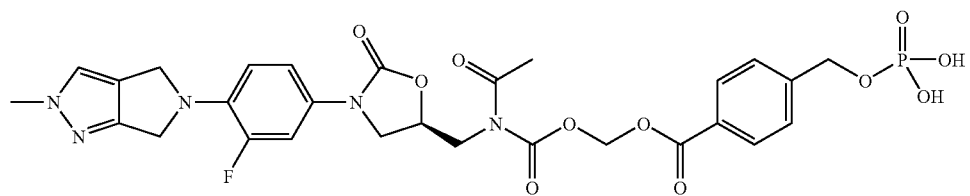
Cpd 16
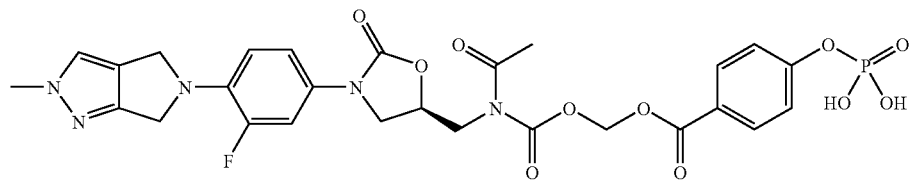
Cpd 18a
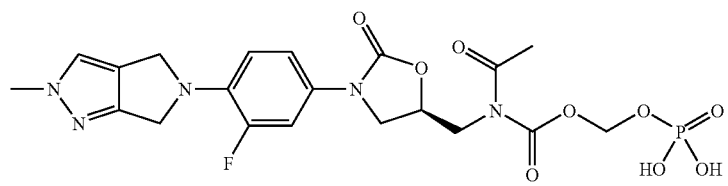
Cpd 18b
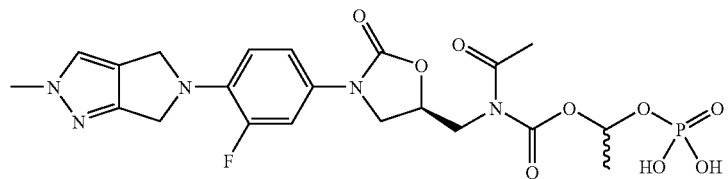
Cpd 21a
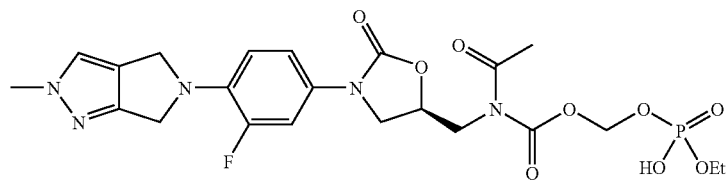

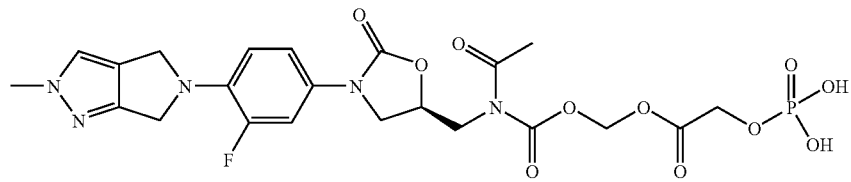

Cpd 24

Abbreviations used in the instant specification and their meanings are as follows:

| Abbreviation | Meaning |
| --- | --- |
| Boc | tert-butoxycarbonyl |
| DCM | dichloromethane |
| DMF | dimethylformamide |
| DMSO | dimethyl sulfoxide |
| Eq or equiv | equivalent |
| EtOAc | ethyl acetate |
| g | grams |
| h | hours |
| HPLC | high performance liquid chromatography |
| M | molar |
| MeOH | methanol |
| mg | milligram |
| min | minutes |
| mL | milliliter |
| HCl | hydrochloric acid |
| MS | mass spectrometry |
| MPLC | medium pressure liquid chromatography |
| N | normal |
| NaHCO$_3$ | sodium bicarbonate |
| NaHMDS | sodium hexamethyldisilazide |
| Na$_2$SO$_4$ | sodium sulfate |
| NH$_4$Cl | ammonium chloride |
| NMR | nuclear magnetic resonance |
| psi | pounds per square inch (gas) |
| rt or RT | room temperature |
| TFA | trifluoroacetic acid |
| THF | tetrahydrofuran |

The compounds of Formula (II) may be prepared from Compound 1, the synthesis of Compound 1 is described in U.S. Pat. No. 6,413,981. Outlined in Schemes 1 through 5 are representative procedures to prepare the compounds of the instant invention.

Scheme 1

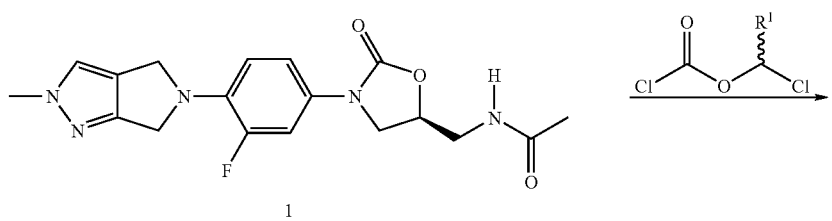

1

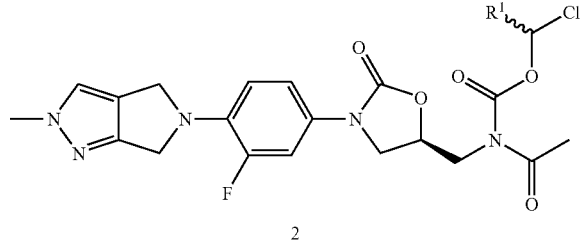

2

Scheme 1 illustrates the method of synthesis of the chloroalkoxycarbonyl precursors (2) to the compounds of the invention. Compound 1 is reacted with a chloroalkyl chloro formate derivative in the presence of a base. Preferred bases include sodium hexamethyldisilazide, potassium hexamethyldisilazide, lithium diisopropylamide (LDA), lithium tetramethylpiperidide, 1,8-diazabicyclo[5.4.0]undec-7-ene (DBU), tetramethylguanidine, and others. The reaction is preferably run for between 30 min to 24 h in an inert solvent such as THF, dioxane, 1,2-dimethoxyethane (DME), or DMF at a temperature ranging from −78° C. to 80° C.

presence of an iodide salt, such as potassium iodide or sodium iodide, in a suitable solvent such as DMF, acetonitrile, or DMSO. The reaction is performed at a temperature ranging from 0° C. to 100° C. for from 2 h to 48 h. If a protecting group is present in the compound of Formula (III), it may optionally be removed by methods known to those skilled in the art to provide compounds of Formula (III) in which the protecting group has been replaced by a hydrogen atom. Amine protecting groups include, but are not limited to, tert-butyloxycarbonyl (Boc), which may be removed under acidic conditions,

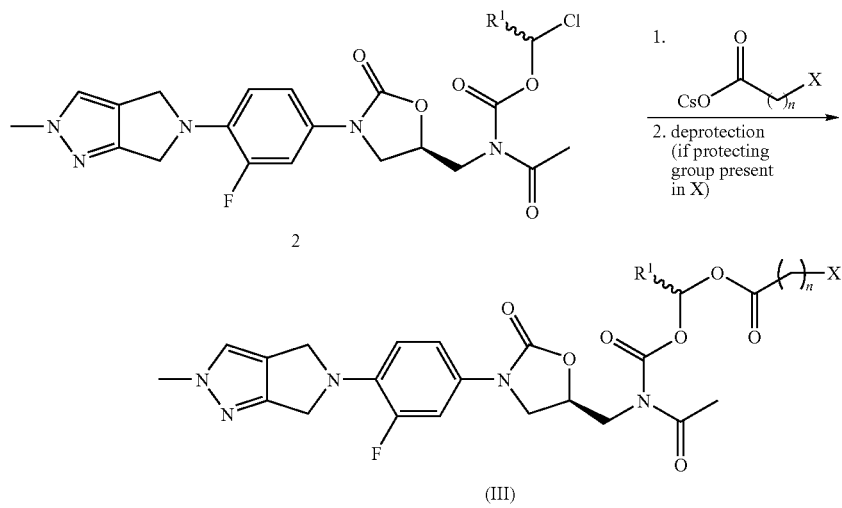

Scheme 2 depicts the conversion of the chloroalkoxycarbonyl derivatives (2) from Scheme 1 to a variety of compounds of the instant invention, including the substituted acyloxymethoxycarbonyl derivatives of Formula (III), wherein $R^1$, X and n are as defined above. As shown in Scheme 2, derivative 2 is reacted with an alkali metal (preferably cesium) salt of an appropriately substituted carboxylic acid derivative. The reaction is optionally performed in the for example by treatment with trifluoroacetic acid in DCM or HCl in ethyl ether, and carbobenzyloxy (Cbz), which may be removed by hydrogenolysis. Phosphate protecting groups include, but are not limited to, tert-butyl ($^t$Bu), which may be removed under acidic conditions, such as by treatment with trifluoroacetic acid in DCM or HCl in ethyl ether, and benzyl (Bn), which may be removed by hydrogenolysis.

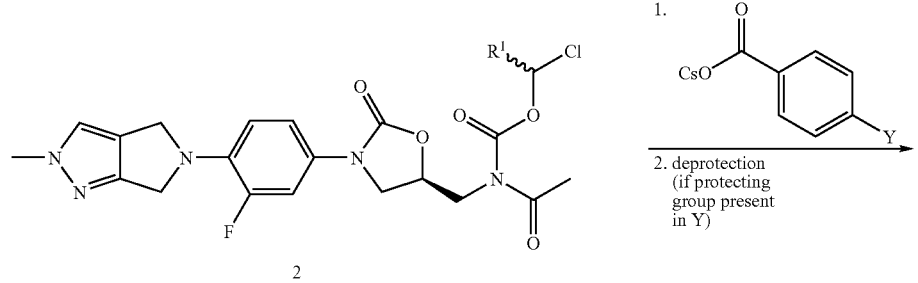

-continued

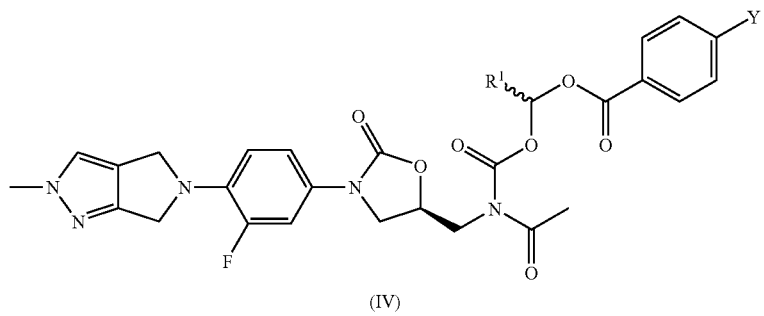

(IV)

Scheme 3 illustrates the synthesis of compounds of Formula IV from derivative Compound 2. The process is similar to the one described in Scheme 2. Derivative Compound 2 is reacted with an alkali metal (preferably cesium) salt of a suitably substituted benzoic acid derivative to provide compounds of Formula (IV). Typically the reaction is conducted in a suitable solvent, such as DMF, acetonitrile, or DMSO at a temperature ranging from 0° C. to 100° C. for from 2 h to 48 h, optionally in the presence of an iodide salt, such as potassium iodide or sodium iodide. If a protecting group is present in the compounds of Formula (IV), it may optionally be removed by methods known to those skilled in the art to provide compounds of Formula (IV) in which the protecting group has been replaced by a hydrogen atom. Phosphate protecting groups include, but are not limited to, tert-butyl ($^t$Bu), which may be removed under acidic conditions, such as by treatment with trifluoroacetic acid in DCM or HCl in ethyl ether, and benzyl (Bn), which may be removed by hydrogenolysis.

Scheme 4 illustrates the synthesis of phosphate ester compounds of Formula (V) from derivative Compound 2. As shown in Scheme 4, derivative Compound 2 is reacted with a suitably protected salt of a phosphoric acid diester derivative. The reaction is optionally performed in the presence of an iodide salt, such as potassium iodide or sodium iodide, in an appropriate solvent, such as DMF, THF, or DMSO. The reaction is preferably performed at a temperature ranging from 0° C. to 100° C. for from 2 h to 96 h, followed by removal of the $PG^1$ protecting group to provide compounds of Formula (V) wherein $R^3$ is lower alkyl. Preferred phosphate salts are those in which $Z^+$ is tetraalkylammonium, which may be prepared by exchange of the t-butylamine salt with a tetraalkylammonium hydroxide derivative. Phosphate protecting groups include, but are not limited to, tert-butyl ($^t$Bu), which may be removed under acidic conditions, such as by treatment with trifluoroacetic acid in DCM or HCl in ethyl ether, and benzyl (Bn), which may be removed by hydrogenolysis.

Scheme 4

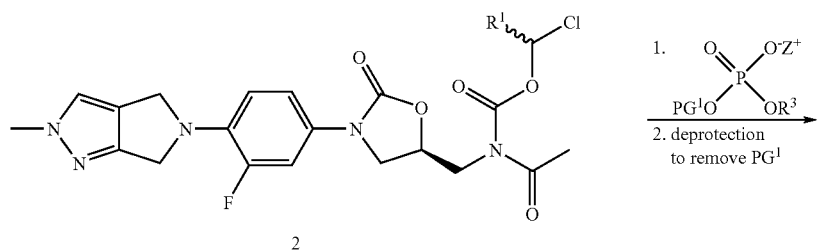

2

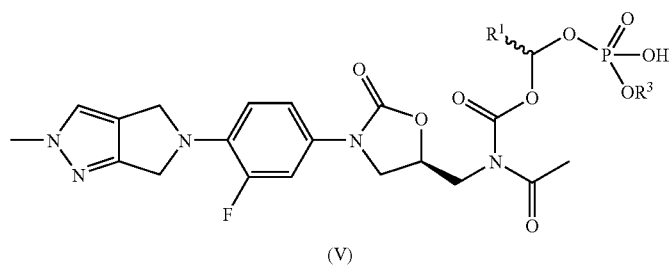

(V)

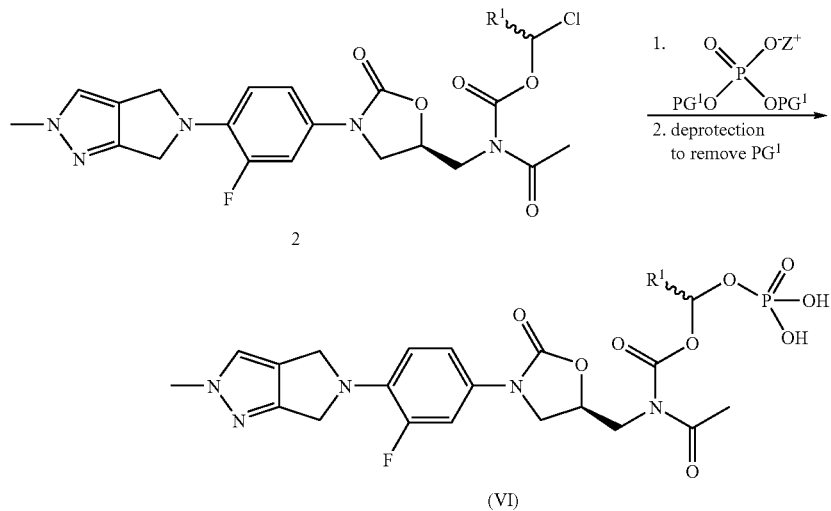

Scheme 5 illustrates the synthesis of phosphate compounds of Formula (VI) from derivative Compound 2. As shown, derivative Compound 2 is reacted with a suitably protected salt of a phosphoric acid diester derivative to produce compounds of Formula (VI). The reaction is optionally performed in the presence of an iodide salt, such as potassium iodide or sodium iodide, in an appropriate solvent, such as DMF, THF, or DMSO, at a temperature ranging from 0° C. to 100° C. for from 2 h to 96 h, followed by removal of the $PG^1$ protecting groups. Preferred phosphate salts are those in which $Z^+$ is tetraalkylammonium. Phosphate protecting groups include, but are not limited to, tert-butyl ($^t$Bu), which may be removed under acidic conditions, such as by treatment with trifluoroacetic acid in DCM or HCl in ethyl ether, and benzyl (Bn), which may be removed by hydrogenolysis.

The following Examples illustrate preferred methods of synthesis for several compounds of Formula (I) and Formula (II).

Example 1

Acetyl-{(R)-3-[3-fluoro-4-(2-methyl-2,6-dihydro-4H-pyrrolo[3,4c]pyrazol-5-yl)-phenyl]-2-oxo-oxazolidin-5-ylmethyl}-carbamic acid chloromethyl ester (2a)

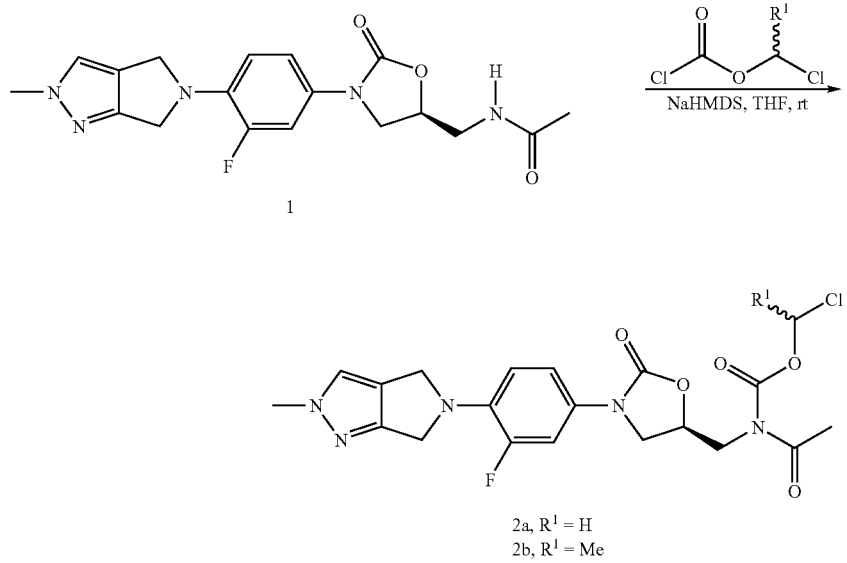

To a suspension of 1 (6.0 g, 16.1 mmol) in anhydrous THF (150 mL) was added NaHMDS (20.9 mL, 20.9 mmol, 1.0 M solution in THF), and the reaction mixture was stirred at rt for 45 min under a nitrogen atmosphere. Chloromethyl chloroformate (1.84 mL, 20.9 mmol) was added and stirring was continued for an additional 45 min. The reaction mixture was quenched with saturated aqueous $NH_4Cl$, and extracted three times with ethyl acetate. The combined organic extracts were dried with $Na_2SO_4$ and concentrated in vacuo. Purification by MPLC ($SiO_2$, 1-10% gradient elution, MeOH:$CH_2Cl_2$) gave 4.29 g (58%) of the title compound as an off white solid. $^1H$ NMR (400 MHz, DMSO-$d_6$): δ 7.54 (s, 1H), 7.43 (dd, 1H), 7.14 (dd, 1H), 6.87 (dd, 1H), 6.03-5.98 (m, 2H), 4.81-4.74 (m, 1H), 4.48-4.46 (m, 4H), 4.15 (dd, 1H), 4.11 (dd, 1H), 3.91 (dd, 1H), 3.85 (s, 3H), 3.78 (dd, 1H), and 2.49 (s, 3H). MS 466 $(M+1)^+$

Example 2

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-chloro-ethyl ester (2b)

To a suspension of 1 (500 mg, 1.34 mmol) in anhydrous THF (8 mL) was added NaHMDS (1.75 mL, 1.75 mmol, 1.0 M solution in THF), and the reaction mixture was stirred at rt for 1 h under a nitrogen atmosphere. Chloroethyl chloroformate (0.18 mL, 1.74 mmol) was added and stirring was continued for an additional 3 h. The reaction mixture was quenched with saturated aqueous $NH_4Cl$, and extracted three times with ethyl acetate. The combined organic extracts were washed with saturated aqueous $NH_4Cl$, dried with $Na_2SO_4$, and concentrated in vacuo. Purification by MPLC (silica, 1-10% gradient elution, MeOH:$CH_2Cl_2$) gave 338 mg (52%) of the title compound as a mixture of diastereomers. $^1H$ NMR (400 MHz, DMSO-$d_6$); δ 7.53 (s, 1H), 7.41 (dd, 1H), 7.17-7.13 (m, 1H), 6.90-6.85 (m, 1H), 6.66-6.60 (m, 1H), 4.82-4.72 (m, 1H), 4.48-4.46 (m, 4H), 4.19-4.07 (m, 2H), 3.96-3.86 (m, 1H), 3.84 (s, 3H), 3.80-3.75 (m, 1H), 2.48 (s, 3H), and 1.84-1.82 (m, 3H). MS 480 $(M+1)^+$

General Procedure A

Preparation of Cesium Salts from the Corresponding Amino Acids

To a solution of amino acid (23.7 mmol) in MeOH (20 mL) and water (10 mL) was added cesium carbonate (11.8 mmol) in small portions. The resulting solution was stirred at rt for 5 min, concentrated in vacuo to remove MeOH, frozen, and then lyophilized to give a white powder. Toluene was added to this powder, and the suspension was concentrated in vacuo, and the resulting white powder was dried in a vacuum oven at 50° C. overnight to give a quantitative yield of cesium salt as a white powder.

Example 3

4-[(Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methoxycarbonylmethyl]-piperazine-1-carboxylic acid tert-butyl ester (3a)

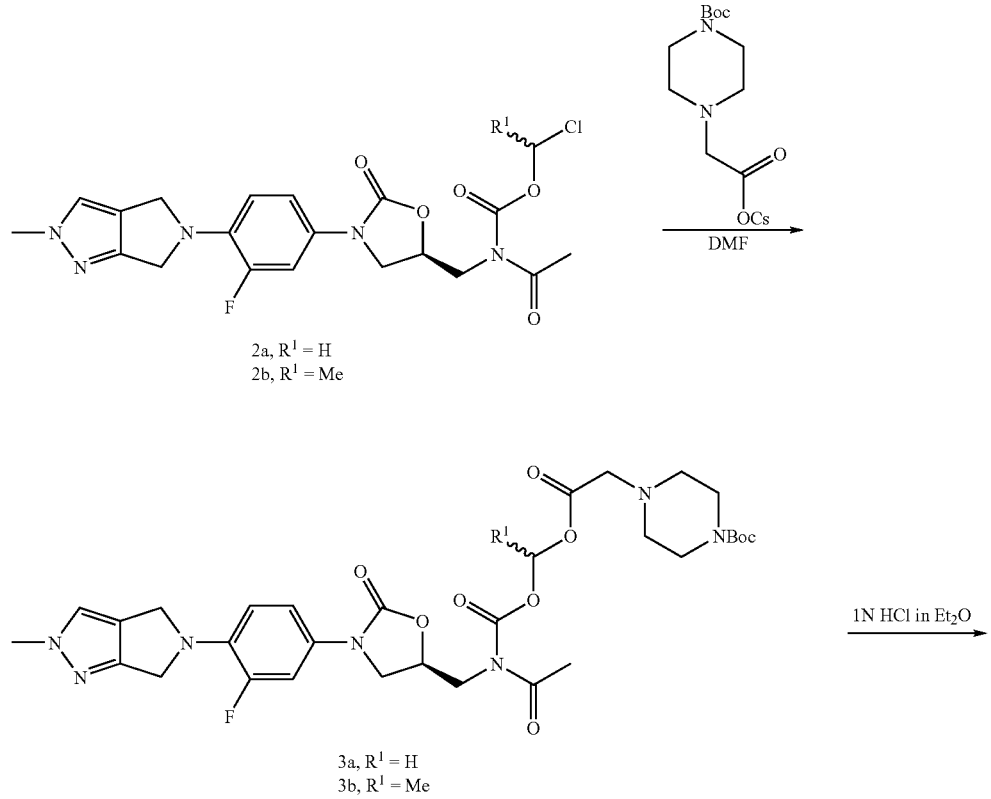

2a, $R^1$ = H
2b, $R^1$ = Me

3a, $R^1$ = H
3b, $R^1$ = Me

-continued

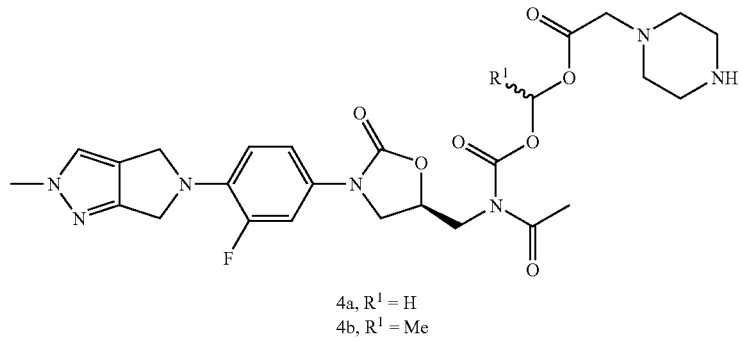

4a, R¹ = H
4b, R¹ = Me

To a solution of 2a (1.41 g, 3.04 mmol) in DMF was added the cesium salt of 4-carboxymethyl-piperazine-1-carboxylic acid tert-butyl ester (1.71 g, 4.56 mol, prepared from 4-carboxymethyl-piperazine-1-carboxylic acid tert-butyl ester following general procedure A) and the resulting suspension was stirred at rt for 20 h and at 40° C. for 2 h. The reaction mixture was then filtered and purified directly by HPLC (C-18 column, 30-90% gradient elution, MeCN:H₂O), and fractions containing product were lyophilized to give 0.670 g, (33%) of the title compound as a fluffy white solid. $^1$H NMR (400 MHz, DMSO-d$_6$): δ 7.53 (s, 1H), 7.42 (dd, 1H), 7.15 (dd, 1H), 6.87 (dd, 1H), 5.83 (s, 2H), 4.78-4.70 (m, 1H), 4.48-4.46 (m, 4H), 4.12-4.06 (m, 2H), 3.89 (dd, 1H), 3.84 (s, 3H), 3.76 (dd, 1H), 3.38 (s, 2H), 3.30-3.28 (m, 4H), 2.47-2.45 (m, 4H), 2.45 (s, 3H), and 1.38 (s, 9H). MS 674 (M+1)$^+$ Example 4

Piperazin-1-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (4a)

To a solution of 3a (1.25 g, 1.85 mmol) in dichloromethane (18 mL) was added dropwise a solution of 1N HCl in diethyl ether (18.5 mL, 18.5 mmol), and the reaction mixture was stirred under nitrogen at rt for 2 h. The reaction mixture was concentrated in vacuo and purified directly by HPLC (C-18 column, 5-55% gradient elution, MeCN:H₂O), to give 0.530 g (53%) of the title compound. $^1$H NMR (400 MHz, DMSO-d$_6$): δ 8.77 (br s, 1H) 7.54 (s, 1H), 7.42 (dd, 1H), 7.15 (dd, 1H), 6.87 (dd, 1H), 5.86-5.83 (m, 2H), 4.78-4.72 (m, 1H), 4.48-4.46 (m, 4H), 4.13-4.06 (m, 2H), 3.90 (dd, 1H), 3.85 (s, 3H), 3.77 (dd, 1H), 3.49 (s, 2H), 3.07-3.04 (m, 4H), 2.78-2.76 (m, 4H), and 2.46 (s, 3H). MS 574 (M+1)$^+$ Example 5

4-[1-(Acetyl-{(R)-3-[3-fluoro-4-(2-methyl-2,6-dihydro-4H-pyrrolo[3,4c]pyrazol-5-yl)-phenyl]-2-oxo-oxazolidin-5-ylmethyl}-carbamoyloxy)-ethoxycarbonylmethyl]-piperazine-1-carboxylic acid tert-butyl ester (3b)

To a solution of 2b (600 mg, 1.26 mmol) in DMF (10 mL) was added the cesium salt of 4-carboxymethyl-piperazine-1-carboxylic acid tert-butyl ester (0.950 g, 2.54 mmol, prepared from 4-carboxymethyl-piperazine-1-carboxylic acid tert-butyl ester following general procedure A) and the resulting suspension was stirred at rt overnight under an atmosphere of nitrogen. The reaction mixture was then filtered and purified directly by HPLC (C-18 column, 30-90% gradient elution, MeCN:H₂O), and fractions containing product were lyophilized to give 95 mg (11%) of the title compound as a mixture of diastereomers. $^1$H NMR (400 MHz, DMSO-d$_6$): δ 7.53 (s, 1H), 7.44-7.39 (m, 1H), 7.17-7.14 (m, 1H), 6.90-6.78 (m, 2H), 4.78-4.70 (m, 1H), 4.48-4.46 (m, 4H), 4.14-4.02 (m, 2H), 3.93-3.87 (m, 1H), 3.84 (s, 3H), 3.78-3.74 (m, 1H), 3.32 (s, 2H), 3.32-3.25 (m, 4H), 2.47-2.42 (m, 7H), 1.52-1.51 (m, 3H), and 1.38-1.37 (m, 9H). MS 688 (M+1)$^+$ Example 6

Piperazin-1-yl-acetic acid 1-(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-ethyl ester (4b)

To a solution of 3b (170 mg, 0.25 mmol) in dichloromethane (18 mL) was added dropwise a solution of 1N HCl in diethyl ether (18.5 mL, 18.5 mmol), and the reaction mixture was stirred under nitrogen at rt for 2 h. The reaction mixture was concentrated in vacuo and purified directly by HPLC (C-18 column, 10-55% gradient elution, MeCN:H₂O), to give 70 mg (48%) of the title compound. $^1$H NMR (400 MHz, DMSO-d$_6$): δ 8.60 (br s, 1H) 7.54 (s, 1H), 7.45-7.40 (m, 1H), 7.17-7.14 (m, 1H), 6.90-6.79 (m, 2H), 4.77-4.71 (m, 1H), 4.48-4.46 (m, 4H), 4.14-4.03 (m, 2H), 3.94-3.89 (m, 1H), 3.85 (s, 3H), 3.79-3.75 (m, 1H), 3.46-3.42 (m, 2H), 3.09-3.05 (m, 4H), 2.78-2.73 (m, 4H), 2.45-2.44 (m, 3H), and 1.53-1.51 (m, 3H). MS 588 (M+1)$^+$

Example 7

Dimethylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (5)

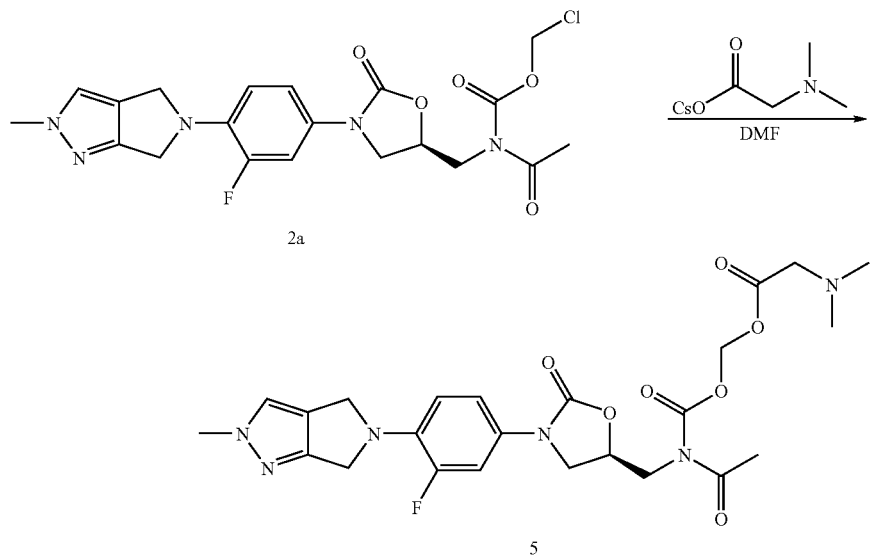

To a solution of 2a (379 g, 0.81 mmol) in DMF (1.6 mL) was added the cesium salt of N,N-dimethyl glycine (192 mg, 0.81 mmol, prepared from N,N-dimethyl glycine following general procedure A) and the resulting suspension was stirred at rt for 24 h. The reaction mixture was filtered, purified directly by HPLC (C-18 column, 30-100% gradient elution, MeCN:H$_2$O), and fractions containing product were lyophilized to give 99 mg (23%) of the title compound as a white powder. $^1$H NMR (400 MHz, DMSO-d$_6$): δ 7.53 (s, 1H), 7.43 (dd, 1H), 7.16 (dd, 1H), 6.87 (dd, 1H), 5.70-5.65 (m, 2H), 4.85-4.78 (m, 1H), 4.48-4.46 (m, 4H), 4.22 (dd, 1H), 4.13 (dd, 1H), 4.00 (dd, 1H), 3.85 (s, 3H), 3.79 (dd, 1H), 3.72 (s, 2H), 3.20 (s, 3H), 3.19 (s, 3H), and 2.50 (s, 3H). MS 533 (M+1)$^+$

Example 8

Morpholin-4-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (6)

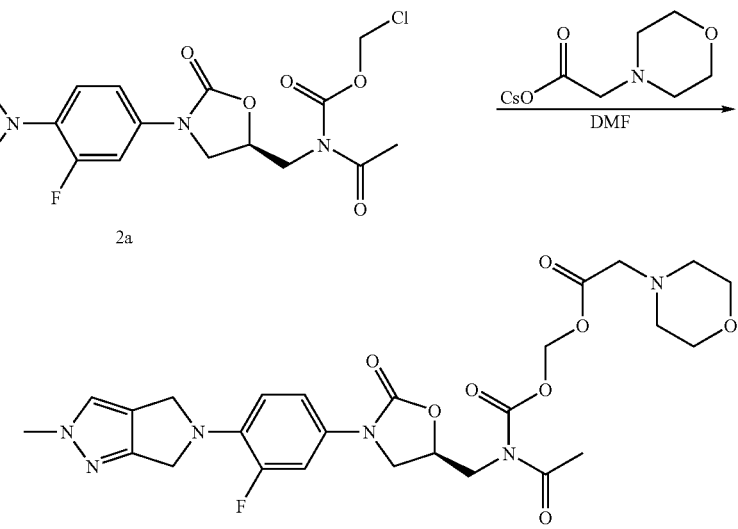

To a solution of 2a (330 mg, 0.71 mmol) in DMF (3.0) mL) was added the cesium salt of morpholine-N-acetic acid (235 mg, 0.85 mmol, prepared from morpholine-N-acetic acid following general procedure A) and the resulting suspension was stirred at rt overnight and at 40° C. for an additional 6 h. The reaction mixture was then filtered and purified directly by HPLC (C-18 column, 30-90% gradient elution, MeCN:H$_2$O), and fractions containing product were lyophilized to give 45 mg, (11%) of the title compound as a white powder. $^1$H NMR (400 MHz, DMSO-d$_6$): δ 7.53 (s, 1H), 7.42 (dd, 1H), 7.15 (dd, 1H), 6.87 (dd, 1H), 5.84 (s, 2H), 4.78-4.71 (m, 1H), 4.48-4.46 (m, 4H), 4.13-4.07 (m, 2H), 3.89 (dd, 1H), 3.85 (s, 3H), 3.76 (dd, 1H), 3.56-3.54 (m, 4H), 3.34 (s, 2H), and 2.45 (s, 3H). MS 575 (M+1)$^+$ Example 9

1-Methyl-pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (7)

To a solution of 2a (300 mg, 0.65 mmol) in DMF (2.5) mL was added the cesium salt of N-methyl-L-proline (335 mg, 1.29 mmol, prepared from N-methyl-L-proline following general procedure A) and the resulting suspension was stirred overnight at rt. The reaction mixture was filtered, purified directly by HPLC (C-18 column, 30-50% gradient elution, MeCN:H$_2$O), and fractions containing product were lyophilized to give 90 mg (25%) of the title compound as mixture of diastereomers (dr 1:1.80). $^1$H NMR (400 MHz, DMSO-d$_6$): δ 7.53 (s, 1H), 7.46-7.40 (m, 1H), 7.17-7.14 (m, 1H), 6.90-6.85 (m, 1H), 6.11-6.04 (m, 1H), 5.42-5.29 (m, 1H), 4.87-4.79 (m, 1H), 4.48-4.46 (m, 4H), 4.27-3.90 (m, 4H), 3.84 (s, 3H), 3.78 (dd, 1H), 3.72-3.35 (m, 2H), 3.23 and 3.08 (two s, 3H), and 2.33-1.91 (m, 4H). MS 559 (M+1)$^+$

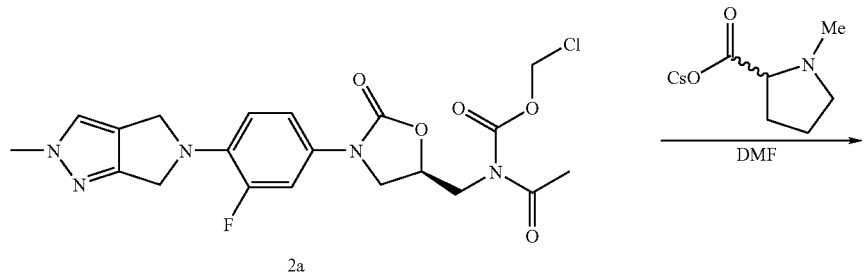

2a

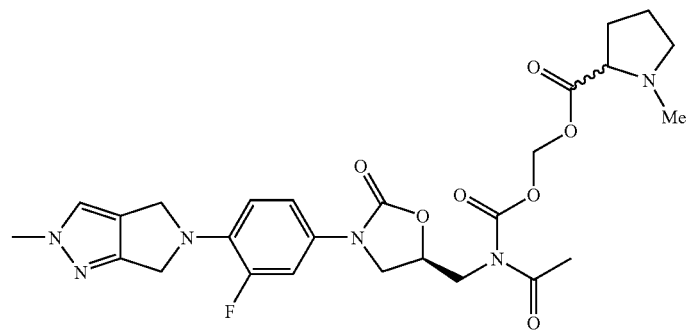

7

Example 10

(4-Methyl-piperazin-1-yl)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (8)

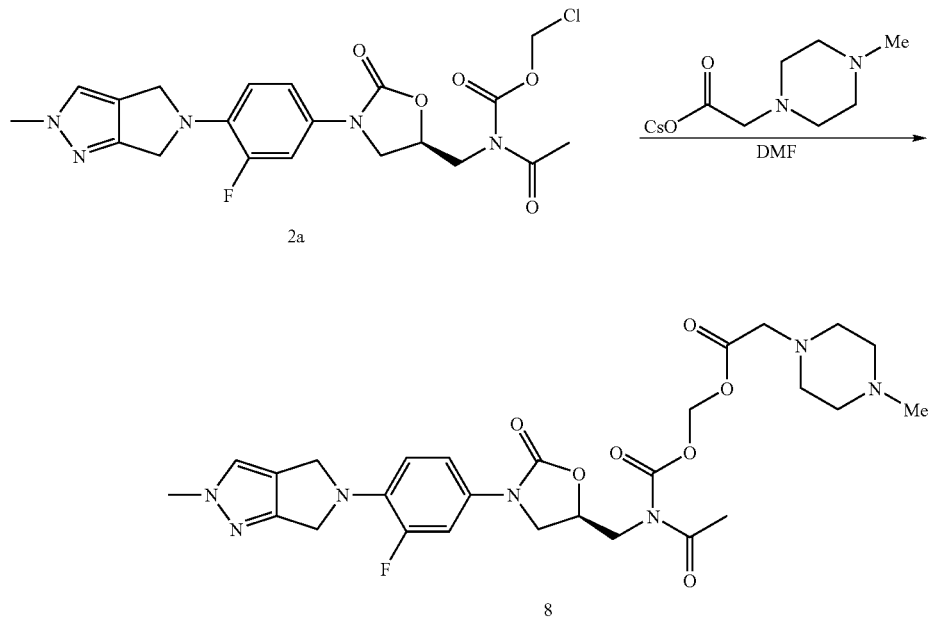

To a solution of 2a (300 mg, 0.65 mmol) in DMF (3.0 mL) was added the cesium salt of (4-methyl-piperazin-1-yl)-acetic acid (379 mg, 1.30 mol, prepared from (4-methyl-piperazin-1-yl)-acetic acid following general procedure A) and the resulting suspension was stirred at rt for 6 h. The reaction mixture was filtered, purified directly by HPLC (C-18 column, 30-80% gradient elution, MeCN:H$_2$O), and fractions containing product were lyophilized to give 80 mg, (21%) of the title compound as a white powder. $^1$H NMR (400 MHz, DMSO-d$_6$): δ 7.53 (s, 1H), 7.42 (dd, 1H), 7.15 (dd, 1H), 6.87 (dd, 1H), 5.83 (s, 2H), 4.78-4.71 (m, 1H), 4.48-4.46 (m, 4H), 4.13-4.07 (m, 2H), 3.89 (dd, 1H), 3.86 (s, 3H), 3.76 (dd, 1H), 3.32 (s, 2H), 2.45 (s, 3H), 2.32-2.24 (m, 4H), and 2.12 (s, 3H). MS 588 (M+1)$^+$

Example 11

(tert-Butoxycarbonyl-methyl-amino)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (9)

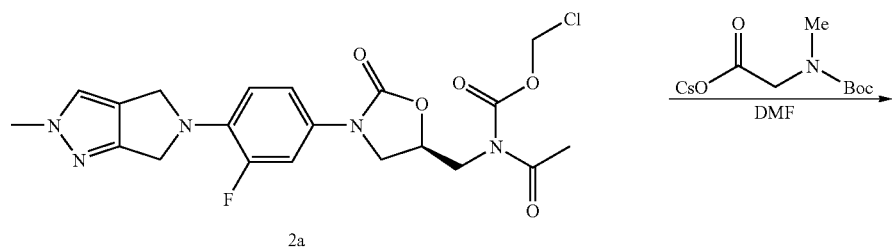

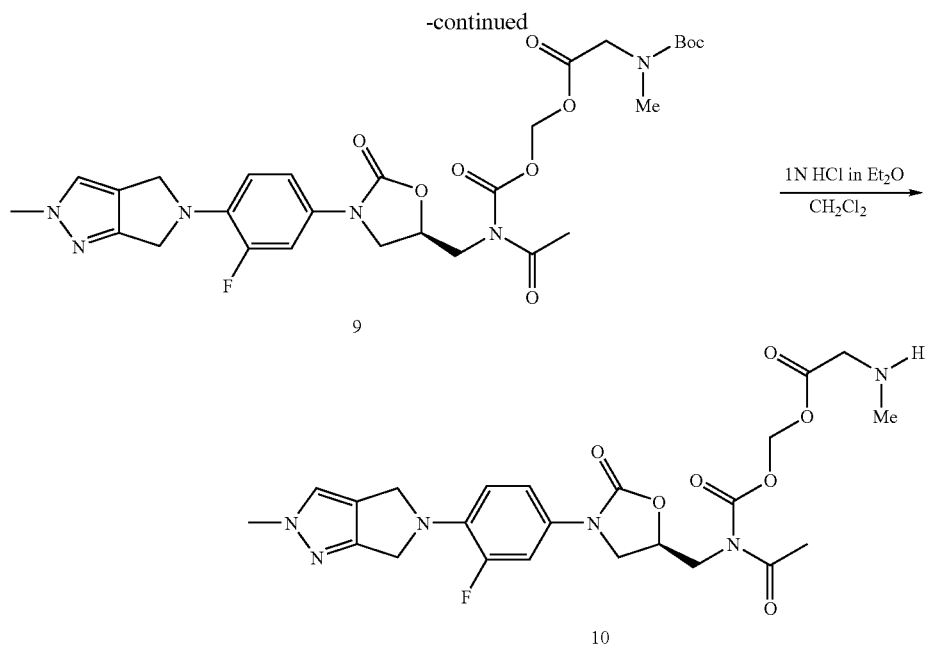

To a solution of 2a (200 mg, 0.43 mmol) in DMF (2 mL) was added the cesium salt of N-Boc sarcosine (276 mg, 0.86 mmol, prepared from N-Boc sarcosine following general procedure A) and the reaction mixture was stirred overnight at rt. The reaction mixture was filtered, purified directly by HPLC (C-18 column, 30-100% gradient elution, MeCN:H$_2$O), and fractions containing product were lyophilized to give 82 mg (31%) of the title compound as a fluffy white solid. $^1$H NMR (400 MHz, DMSO-d$_6$): observed as a mixture of rotomers. δ 7.53 (s, 1H), 7.42 (dd, 1H), 7.15 (dd, 1H), 6.87 (dd, 1H), 5.88-5.86 (m, 2H), 4.79-4.71 (m, 1H), 4.48-4.46 (m, 4H), 4.15-4.08 (m, 2H), 4.06 (br s, 2H), 3.92-3.86 (m, 1H), 3.85 (s, 3H), 3.78 (dd, 1H), 2.86 and 2.82 (two s, 3H), 2.46 (s, 3H), 1.38 and 1.32 (two s, 9H). MS 619 (M+1)$^+$ Example 12

Methylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (10)

To a solution of 9 (50 mg, 0.08 mmol) in CH$_2$Cl$_2$ (2 mL) under nitrogen was added 1N HCl in Et$_2$O (2.0 mL, 2.0 mmol). The reaction mixture was stirred at rt for 2 h, concentrated in vacuo, and purified directly by HPLC (C-18 column, 30-80% gradient elution, MeCN:H$_2$O with 0.1% TFA). Fractions containing product were lyophilized to give 15 mg (36%) of the title compound as the trifluoroacetate salt. $^1$H NMR (400 MHz, DMSO-d$_6$): δ 9.07 (br s, 1H), 7.54 (s, 1H), 7.43 (dd, 1H), 7.16 (dd, 1H), 6.87 (dd, 1H), 5.96-5.92 (m, 2H), 4.80-4.74 (m, 1H), 4.48-4.46 (m, 4H), 4.15-4.09 (m, 4H), 3.91 (dd, 1H), 3.85 (s, 3H), 3.76 (dd, 1H), 2.62 (s, 3H), 2.47 (s, 3H). MS 519 (M+1)$^+$ Example 13

(S)-Pyrrolidine-1,2-dicarboxylic acid 2-[(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl]ester 1-tert-butyl ester (11)

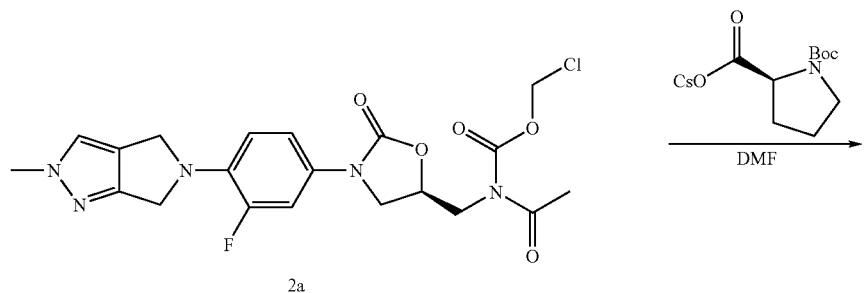

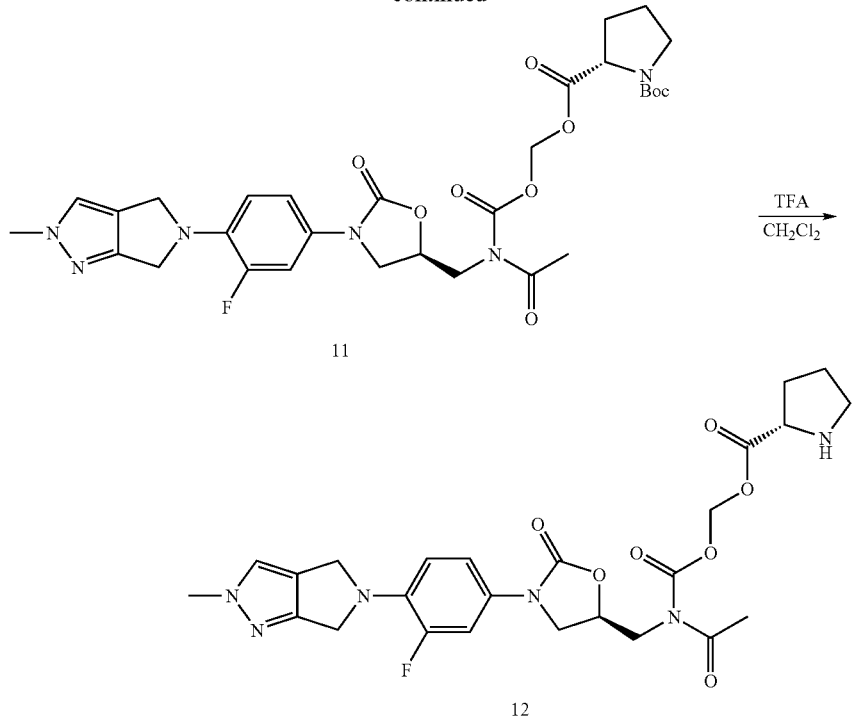

To a solution of 2a (300 mg, 0.65 mmol) in DMF (2.5 mL) was added the cesium salt of N-Boc-L-proline (291 mg, 0.84 mmol, prepared from N-Boc-L-proline following general procedure A) and the reaction mixture was stirred overnight at rt. The reaction mixture was filtered, purified directly by HPLC (C-18 column, 30-90% gradient elution, MeCN:H$_2$O), and fractions containing product were lyophilized to give 243 mg (59%) of the title compound as a fluffy white solid. $^1$H NMR (400 MHz, CDCl$_3$): δ 7.39-7.34 (m, 1H), 7.14 (s, 1H), 7.11-7.06 (m, 1H), 6.71-6.66 (m, 1H), 5.91 (s, 2H), 4.85-4.76 (m, 1H), 4.57-4.56 (m, 4H), 4.33-4.17 (m, 2H), 4.09-3.98 (m, 2H), 3.93 (s, 3H), 3.70-3.64 (m, 1H), 3.58-3.37 (m, 2H), 2.56 (s, 3H), 2.33-2.20 (m, 1H), 2.05-1.86 (m, 3H), 1.42 and 1.40 (two s, 9H). MS 645 (M+1)$^+$ Prophetic Example 14

(S)-Pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (12)

To a solution of 11 (1 equiv) in dichloromethane at rt under nitrogen is added TFA (5 equiv) dropwise. The reaction mixture is stirred at rt for 2 h, concentrated in vacuo, purified directly by HPLC (C-18 column, 0-100% gradient elution, MeCN:H$_2$O with 0.1% TFA), and fractions containing product are lyophilized to give the title compound. Theoretical MS 545 (M+1)$^+$ Example 15

4-(Bis-benzyloxy-phosphoryloxymethyl)-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (13)

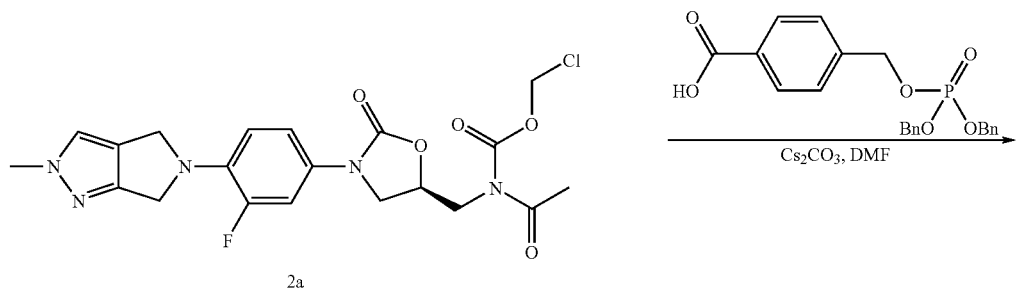

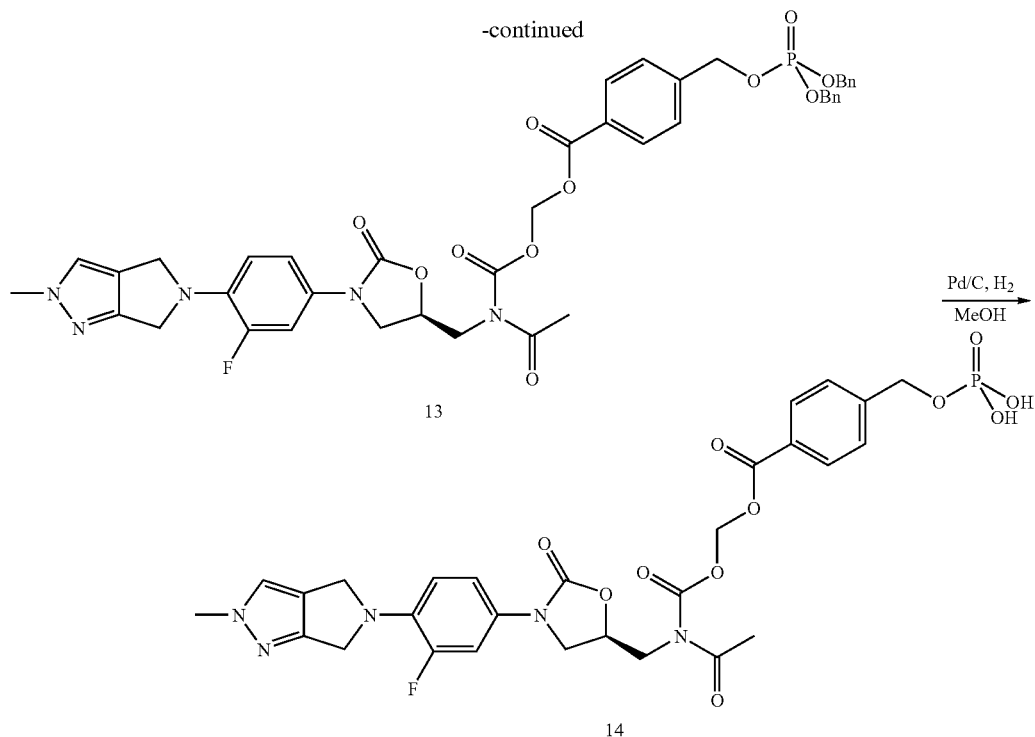

To a solution of 4-[[[bis(phenylmethoxy)phosphinyl]oxy]methyl]-benzoic acid (69 mg, 0.17 mmol, prepared according to the procedure described in Zhu, Z.; Chen, H.; Goel, O. P.; Chan, O. H.; Stilgenbauer, L. A.; Stewart, B. H. *Bioorg Med. Chem. Lett.* 2000, 10, 1121) in DMF (0.6 mL) was added cesium carbonate (22 mg, 0.06 mmol) and the reaction mixture was stirred at rt for 1 h. To this mixture was added 2a and stirring was continued overnight. The crude reaction mixture was filtered, purified directly by HPLC (C-18 column, 30-100% gradient elution, MeCN:H$_2$O), and fractions containing product were lyophilized to give 38 mg (35%) of the title compound. $^1$H NMR (400 MHz, DMSO-d$_6$): δ 8.00 (d, 2H), 7.52 (s, 1H), 7.50 (d, 2H), 7.38-7.33 (m, 11H), 7.12 (dd, 1H), 6.83 (dd, 1H), 6.09-6.06 (m, 2H), 5.13 (d, 2H), 5.05 (d, 4H), 4.80-4.73 (m, 1H), 4.47-4.45 (m, 4H), 4.15-4.06 (m, 2H), 3.92 (dd, 1H), 3.84 (s, 3H), 3.78 (dd, 1H), 2.47 (s, 3H). MS 842 (M+1)$^+$ Prophetic Example 16

4-Phosphonooxymethyl-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (14)

A suspension of 13 (1 equiv) and 10% Pd/C (1 weight equiv of 13) in methanol is hydrogenated in a Parr shaker at 30 psi for 6 h. The reaction mixture is filtered, concentrated in vacuo, purified directly by HPLC (C-18 column, 0-100% gradient elution, MeCN:H$_2$O), and fractions containing product are lyophilized to give the title compound. Theoretical MS 662 (M+1)$^+$ Example 17

4-(Bis-benzyloxy-phosphoryloxy)-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (15)

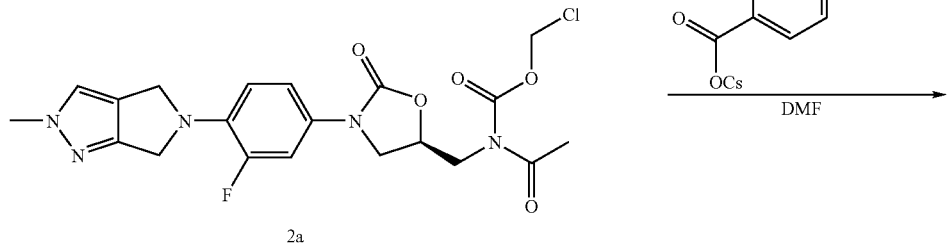

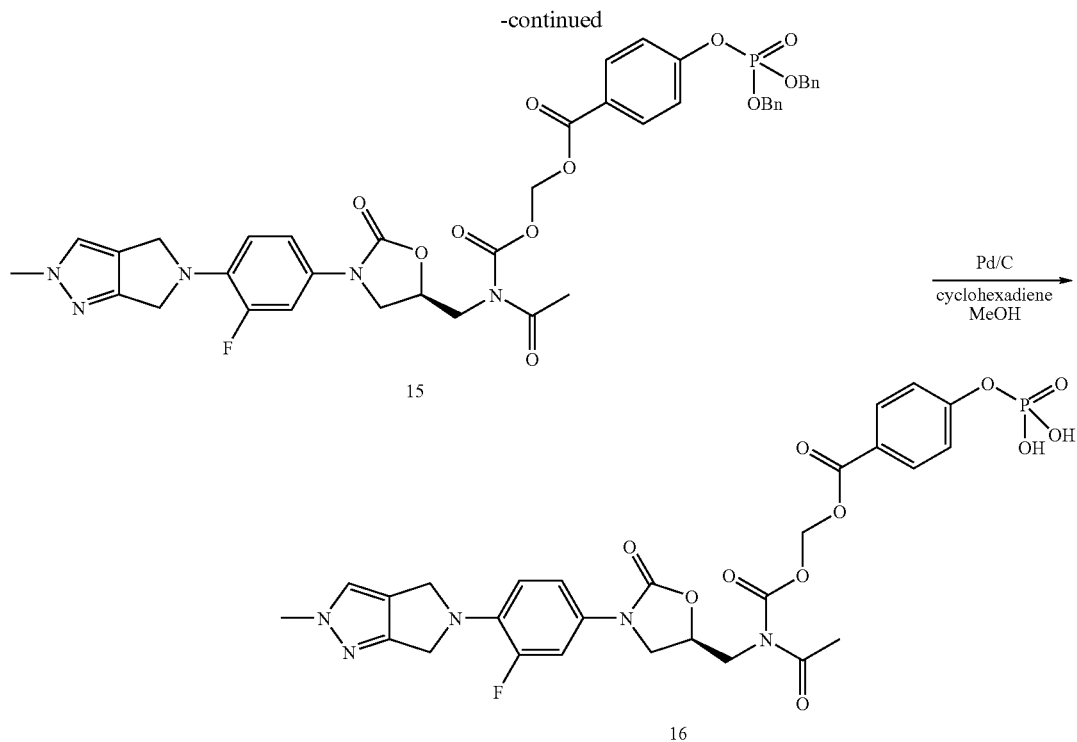

To a solution of 2a (232 mg, 0.50 mmol) in DMF (1.5 mL) was added the cesium salt of 4-(bis-benzyloxy-phosphoryloxy)-benzoic acid (397 mg, 0.75 mmol; 4-(bis-benzyloxy-phosphoryloxy)-benzoic acid was prepared following the procedure described in WO 2001027106. The cesium salt of 4-(bis-benzyloxy-phosphoryloxy)-benzoic acid was prepared using general procedure A). The reaction mixture was stirred overnight at rt, filtered, and purified directly by HPLC (C-18 column, 30-100% gradient elution, MeCN:H$_2$O). Fractions containing product were lyophilized to give 85 mg (21%) of the title compound as a fluffy white solid. $^1$H NMR (400 MHz, DMSO-d$_6$): δ 8.03 (d, 2H), 7.52 (s, 1H), 7.42-7.33 (m, 13H), 7.11 (dd, 1H), 6.83 (dd, 1H), 6.07-6.04 (m, 2H), 5.18 (d, 4H), 4.80-4.73 (m, 1H), 4.47-4.45 (m, 4H), 4.15-4.07 (m, 2H), 3.92 (dd, 1H), 3.84 (s, 3H), 3.76 (dd, 1H), 2.47 (s, 3H). MS 828 (M+1)$^+$ Prophetic Example 18

4-Phosphonooxy-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (16)

A suspension of 15 (1 equiv) and 10% Pd/C (1 weight equiv of 15) in 1,4-cyclohexadiene and THF is stirred at rt for 6 h. The reaction mixture is filtered, concentrated in vacuo, purified directly by HPLC (C-18 column, 0-100% gradient elution, MeCN:H$_2$O), and fractions containing product are lyophilized to give the title compound. Theoretical MS 646 (M+1)$^+$ Example 19

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid di-tert-butoxy-phosphoryloxymethyl ester (17a)

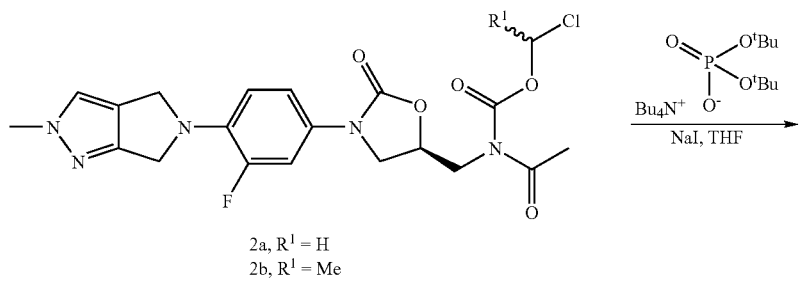

2a, R$^1$ = H
2b, R$^1$ = Me

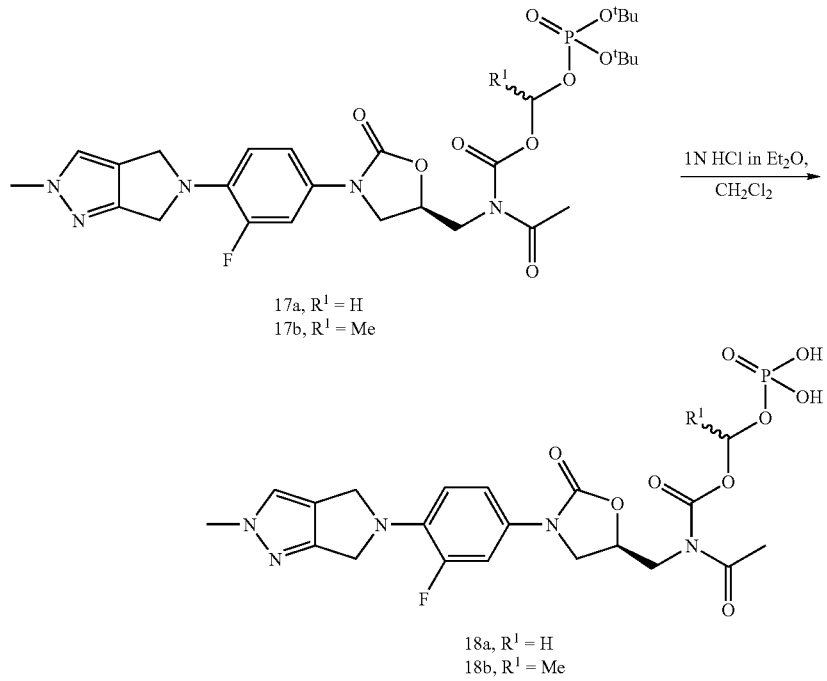

17a, R¹ = H
17b, R¹ = Me

18a, R¹ = H
18b, R¹ = Me

To a solution of 2a (1.545 g, 3.33 mmol) in THF (25 mL) was added sodium iodide (549 mg, 3.66 mmol) and the tetrabutylammonium salt of di-tert-butylphosphate (1.545 g, 3.42 mmol). The reaction mixture was heated at 65° C. for 24 h, concentrated in vacuo, dissolved in DMSO, filtered, and purified directly by HPLC (C-18 column, 30-100% gradient elution, MeCN:H$_2$O). Fractions containing product were lyophilized to give 1.07 g (50%) of the title compound. $^1$H NMR (400 MHz, DMSO-d$_6$): δ 7.53 (s, 1H), 7.42 (dd, 1H), 7.16 (dd, 1H), 6.87 (dd, 1H), 5.68 (dd, 1H), 5.60 (dd, 1H), 4.85-4.78 (m, 1H), 4.48-4.46 (m, 4H), 4.19-4.08 (m, 2H), 3.90 (dd, 1H), 3.84 (s, 3H), 3.79 (dd, 1H), 2.49 (s, 3H), 1.42 (s, 18H). MS 1301 (2M+23)$^+$

Example 20

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(di-tert-butoxy-phosphoryloxy)-ethyl ester (17b)

To a solution of 2b (75 mg, 0.16 mmol) in THF (1.5 mL) was added sodium iodide (66 mg, 0.44 mmol) and the tetrabutylammonium salt of di-tert-butylphosphate (200 mg, 0.04 mmol). The reaction mixture was heated at 65° C. for 48 h, concentrated in vacuo, dissolved in DMSO, filtered, and purified directly by HPLC (C-18 column, 30-100% gradient elution, MeCN:H$_2$O). Fractions containing product were lyophilized to give 20 mg (20%) of the title compound as a 1:1 mixture of diastereomers. $^1$H NMR (400 MHz, DMSO-d$_6$): δ 7.53 (s, 1H), 7.44-7.39 (m, 1H), 7.17-7.14 (m, 1H), 6.90-6.85 (m, 1H), 6.45-6.38 (m, 1H), 4.85-4.75 (m, 1H), 4.48-4.46 (m, 4H), 4.25-4.08 (m, 2H), 3.95-3.77 (m, 2H), 3.85 (s, 3H), 2.47-2.48 (m, 3H), 1.56-1.54 (m, 3H), 1.41-1.40 (m, 18H). MS 654 (M+1)$^+$

Example 21

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid phosphonooxymethyl ester (18a)

To a solution of 17a (500 mg, 0.78 mmol) in dichloromethane (2.5 mL) under an atmosphere of nitrogen was added a solution of 1N HCl in diethyl ether (2.34 mL, 2.34 mmol) and the reaction mixture was stirred at rt for 3 h. The reaction mixture was concentrated in vacuo, purified directly by HPLC (C-18 column, 10-100% gradient elution, MeCN: H$_2$O), and fractions containing product were lyophilized to give 290 mg (70%) of the title compound. $^1$H NMR (400 MHz, DMSO-d$_6$): δ 7.53 (s, 1H), 7.42 (dd, 1H), 7.16 (dd, 1H), 6.87 (dd, 1H), 5.65 (dd, 1H), 5.58 (dd, 1H), 4.87-4.80 (m, 1H), 4.48-4.46 (m, 4H), 4.20 (dd, 1H), 4.09 (dd, 1H), 3.87 (dd, 1H), 3.84 (s, 3H), 3.78 (dd, 1H), and 2.49 (s, 3H). MS 528 (M+1)$^+$

Prophetic Example 22

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-phosphonooxy-ethyl ester (18b)

To a solution of 17b (1 equiv) in dichloromethane is added TFA (3 equiv) and the reaction mixture is stirred at rt for 3 h. The reaction mixture is concentrated in vacuo, and purified directly by HPLC (C-18 column, 10-100% gradient elution, MeCN:H$_2$O) to give the title compound. Theoretical MS 542 (M+1)$^+$

Example 23

Tetrabutyl Ammonium Salt of Phosphoric Acid Benzyl Ester Ethyl Ester (19)

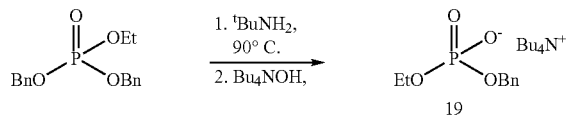

The first step in this reaction sequence was carried out according to a procedure described in Gray, M. D. M.; Smith, D. J. H. *Tetrahedron. Lett.* 1980, 21, 859. A solution of phosphoric acid dibenzyl ester ethyl ester (5.22 g, 17.05 mmol) in tert-butylamine (10 mL) was heated at 92° C. (oil bath temperature) in a sealed tube for 8 h. Upon cooling to rt a white waxy solid formed. To this solid was added tetrabutylammonium hydroxide (11.37 mL, 17.05 mmol) and the resulting homogenous solution was extracted three times with diethyl ether. The aqueous layer was concentrated in vacuo and dried under a vacuum overnight to give 7.53 g (96%) of a pale brown oil, which was used in the next step without further purification. $^1$H NMR (400 MHz, DMSO-$d_6$): δ 7.33-7.20 (m, 5H), 4.63 (d, 2H), 3.65-3.58 (m, 2H), 3.19-3.15 (m, 8H), 1.60-1.53 (m, 8H), 1.35-1.26 (m, 8H), 1.05 (t, 3H), and 0.93 (t, 12H).

Example 24

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid benzyloxy-ethoxy-phosphoryloxymethyl ester (20a)

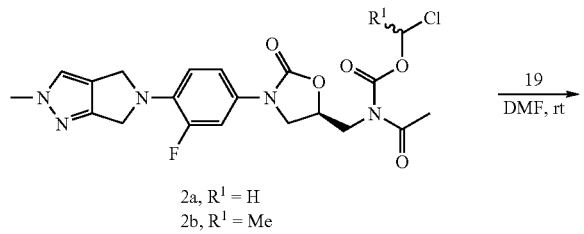

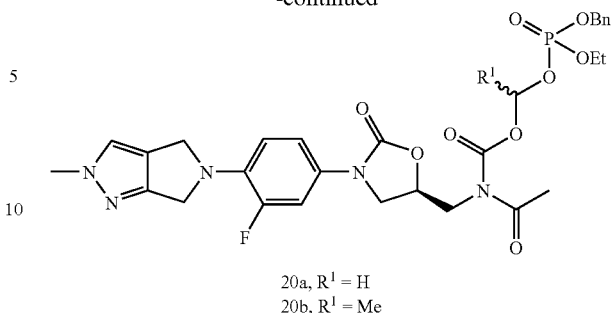

To a solution 2a (3.96 g, 8.52 mmol) in DMF (12 mL) was added phosphate derivative 19 (7.53 g, 17.05 mmol). The reaction mixture was stirred at rt for 48 h, filtered, and purified directly by HPLC (C-18 column, 50-80% gradient elution, MeCN:H$_2$O) to give 1.20 g (22%) of the title compound as a fluffy white powder. $^1$H NMR (400 MHz, DMSO-$d_6$): δ 7.54 (s, 1H), 7.44-7.34 (m, 6H), 7.16-7.13 (m, 1H), 6.89-6.84 (m, 1H), 5.77-5.66 (m, 2H), 5.08 (d, 2H), 4.81-4.73 (m, 1H), 4.48-4.46 (m, 4H), 4.14-4.04 (m, 4H), 3.87-3.82 (m, 4H), 3.77-3.73 (m, 1H), 2.44 and 2.43 (two s, 3H), 1.22 (dt, 3H). MS 646 (M+1)$^+$

Prophetic Example 25

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(benzyloxy-ethoxy-phosphoryloxy)-ethyl ester (20b)

To a solution 2b (1 equiv.) in DMF is added phosphate derivative 19 (2 equiv.). The reaction mixture is stirred at rt for 48 h, filtered, and purified directly by HPLC (C-18 column, 50-80% gradient elution, MeCN:H$_2$O) to give the title compound. Theoretical MS 660 (M+1)$^+$

Example 26

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid ethoxy-hydroxy-phosphoryloxymethyl ester (21a)

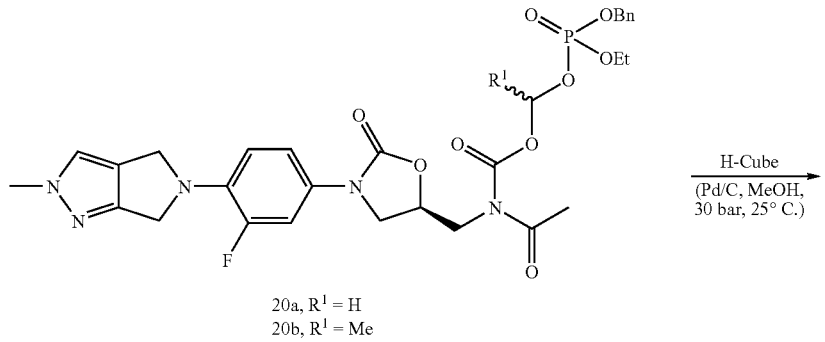

-continued

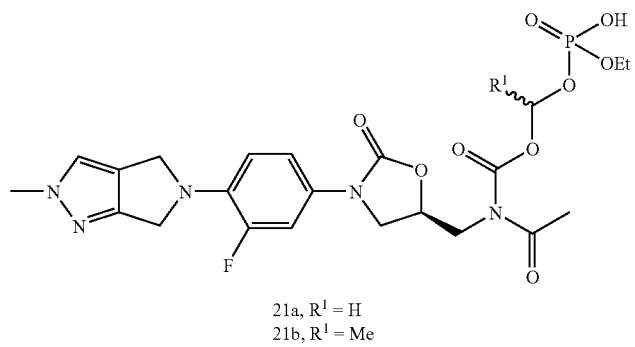

21a, R¹ = H
21b, R¹ = Me

A solution of 20a (1.20 g, 1.86 mmol) in methanol (40 mL) was passed through an "H-cube" hydrogenator equipped with a 10% Pd on carbon cartridge under 30 bar of hydrogen at a flow rate of 1 mL/min. The reaction mixture was concentrated in vacuo and purified directly by HPLC (C-18 column, 5-55% gradient elution, MeCN:H₂O). Fractions containing product were lyophilized to give 555 mg (54%) of the title compound as a fluffy white solid. ¹H NMR (400 MHz, DMSO-d₆): δ 7.54 (s, 1H), 7.43 (dd, 1H), 7.17 (dd, 1H), 6.87 (dd, 1H), 5.70-5.57 (m, 2H), 4.86-4.79 (m, 1H), 4.48-4.46 (m, 4H), 4.18 (dd, 1H), 4.10 (t, 1H), 3.99-3.91 (m, 2H), 3.88 (dd, 1H), 3.85 (s, 3H), 3.79 (dd, 1H), 2.49 (s, 3H), 1.20 (t, 3H). MS 556 (M+1)⁺

Prophetic Example 27

Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(ethoxy-hydroxy-phosphoryloxy)-ethyl ester (21b)

A solution of 20b (1 equiv.) in methanol is passed through an "H-cube" hydrogenator equipped with a 10% Pd on carbon cartridge under 30 bar of hydrogen at a flow rate of 1 mL/min. The reaction mixture is concentrated in vacuo and purified directly by HPLC (C-18 column, 5-55% gradient elution, MeCN:H₂O) to give the title compound. Theoretical MS 570 (M+1)⁺

Example 28

Cesium salt of (di-tert-butoxy-phosphoryloxy)-acetic acid (22)

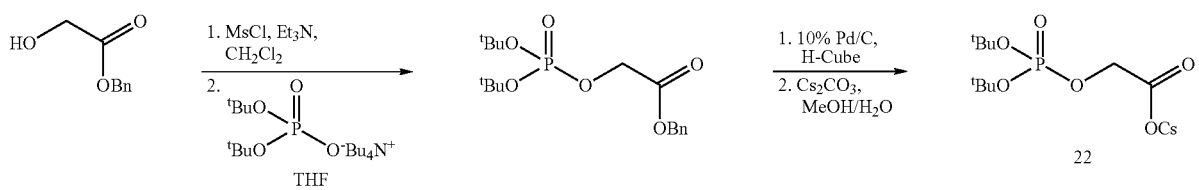

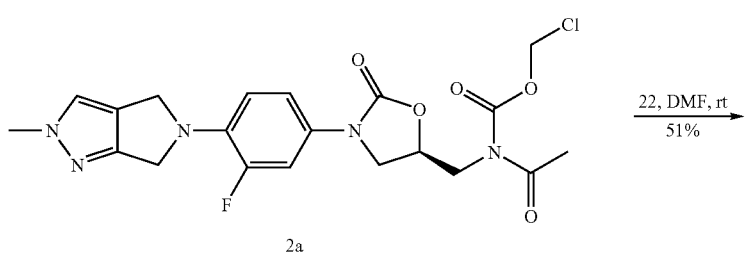

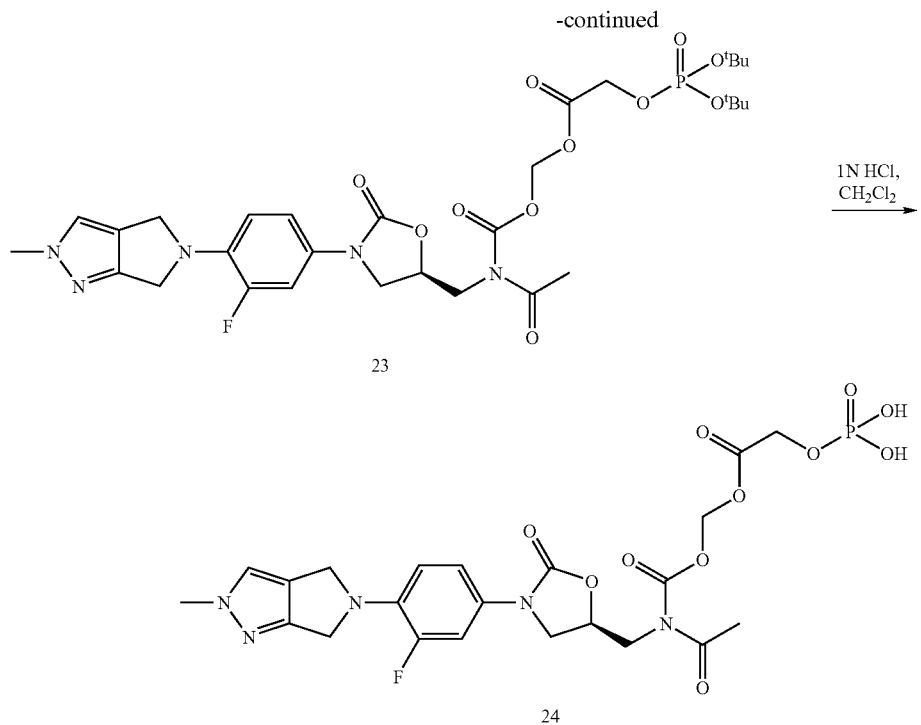

Step 1: To a solution of benzyl glycolate (2.0 mL, 14.1 mmol) and triethylamine (2.35 mL, 16.9 mmol) in dichloromethane (30 mL) at 0° C. was added dropwise methanesulfonyl chloride (1.20 mL, 15.1 mL). The reaction was stirred overnight, diluted with dichloromethane, washed with saturated aqueous NH$_4$Cl, and then with saturated NaHCO$_3$, dried with Na$_2$SO$_4$, and concentrated in vacuo to give 2.50 g (73%) of methanesulfonyloxy-acetic acid benzyl ester which was used in the next step without further purification.

Step 2: To a solution of methanesulfonyloxy-acetic acid benzyl ester (2.50 g, 10.24 mmol) in THF (20 mL) was added the tetrabutylammonium salt of di-tert-butylphosphate (4.61 g, 10.24 mmol). The reaction was stirred overnight, concentrated, and purified directly by MPLC (SiO$_2$, 10-30% gradient elution, Hexane: EtOAc) to give 1.42 g (39%) of (di-tert-butoxy-phosphoryloxy)-acetic acid benzyl ester. $^1$H NMR (400 MHz, CDCl$_3$): δ 7.37-7.35 (m, 5H), 5.21 (s, 2H), 4.55 (d, 2H), and 1.48 (s, 18H).

Step 3: (Di-tert-butoxy-phosphoryloxy)-acetic acid benzyl ester (700 mg, 1.96 mmol) was dissolved in MeOH (40 mL) and passed through a "H-cube" hydrogenator with a 10% Pd on carbon cartridge under 40 psi of hydrogen at a flow rate of 1 mL/min. The reaction mixture was concentrated in vacuo to give 513 mg (98%) of (di-tert-butoxy-phosphoryloxy)-acetic acid, which was used in the next step without further purification. $^1$H NMR (400 MHz, CDCl$_3$): δ 4.53 (d, 2H), and 1.51 (s, 18H).

Step 4: To a solution of (di-tert-butoxy-phosphoryloxy)-acetic acid (480 mg, 1.79 mmol) in MeOH (4 mL) and water (2 mL) was added cesium carbonate (261 mg, 0.80 mmol) and the reaction was stirred at rt for 10 min. The resulting homogenous solution was concentrated in vacuo to give the title compound as a gummy solid.

Example 29

(Di-tert-butoxy-phosphoryloxy)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (23)

To a solution of 2a (579 mg, 1.24 mmol) in DMF (2.5 mL) was added 22 (1.49 g, 3.73 mmol) and the reaction mixture was stirred overnight at rt. The reaction mixture was filtered, purified directly by HPLC (C-18 column, 30-100% gradient elution, MeCN:H$_2$O), and fractions containing product were lyophilized to give 438 mg (51%) of the title compound as a fluffy white solid. $^1$H NMR (400 MHz, DMSO-d$_6$): δ 7.53 (s, 1H), 7.42 (dd, 1H), 7.14 (dd, 1H), 6.87 (dd, 1H), 5.89 (s, 2H), 4.80-4.72 (m, 1H), 4.60 (d, 2H), 4.48-4.46 (m, 4H), 4.14-4.08 (m, 2H), 3.89 (dd, 1H), 3.85 (s, 3H), 3.76 (dd, 1H), 2.46 (s, 3H), and 1.41 (s, 18H). MS 698 (M+1)$^+$ Example 30

Phosphonooxy-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester (24)

To a solution of 23 (20 mg, 0.03 mmol) in dichloromethane (1 mL) under nitrogen was added dropwise a solution of 1N HCl in diethyl ether (2.0 mL, 2.0 mmol). The reaction mixture was stirred for 1 h at rt, concentrated in vacuo, and purified directly by HPLC (C-18 column, 10-70% gradient elution, MeCN:H$_2$O with 0.1% TFA) to give 5 mg (25%) of the title compound. $^1$H NMR (400 MHz, DMSO-d$_6$): δ 7.53 (s, 1H), 7.42 (dd, 1H), 7.15 (dd, 1H), 6.87 (dd, 1H), 5.88 (s, 2H), 4.79-4.72 (m, 1H), 4.53 (d, 2H), 4.48-4.46 (m, 4H), 4.15-4.07 (m, 2H), 3.88 (dd, 1H), 3.85 (s, 3H), 3.76 (dd, 1H), and 2.46 (s, 3H). MS 586 (M+1)$^+$ Prodrug Solubility One mg of each compound was diluted with at least 100 µl of the designated buffer, vortexed vigorously for approximately 1 minute, and visually inspected. Sodium citrate (40 mM) was buffered to pH 4 and phosphate-buffered saline was buffered to pH 7. Solutions with no remaining particles were recorded with a solubility ≧to the starting concentration. Compound suspensions were further diluted in 0.1 mL increments followed by vortexing as above, until the prodrug was dissolved. The solubility of the prodrugs in the buffers tested is listed in Table 1. Solubilities of prodrugs ranged from 1.0 mg/ml to >10 mg/ml. The term "ND" means not determined.

TABLE 1

| Compound | Solubility | |
|---|---|---|
| | Sodium Citrate | Saline |
| 4a | ≧10 mg/mL | ≧10/mg/mL |
| 4b | ≧7.5 mg/mL | ND |
| 5 | ≧10 mg/mL | ≧10 mg/mL |
| 6 | 2.5 mg/mL | 1.0 mg/mL |
| 8 | ≧10 mg/mL | ≧10/mg/mL |
| 10 | ≧10 mg/mL | ≧10 mg/mL |
| 18a | ≧2 mg/mL | ≧2 mg/mL |
| 21a | ≧10 mg/mL | ≧10/mg/mL |
| 24 | ≧5 mg/mL | ND |

The solubility of the active drug, Compound 1, was determined in a separate experiment in which an excess of the compound was added to pH 4 buffer. The mixture was shaken with a Burrell wrist action shaker at ambient temperature for 24 hours. Excess solute was removed by centrifugation, the supernatant was diluted with a suitable solvent, and the concentration of the compound was measured using HPLC. The solubility of Compound 1 at pH 4 was 0.007 mg/mL.

Evaluation of Prodrug Efficacy in a Mouse Systemic Lethal Infection Model

Female Swiss Webster mice weighing between 20-25 g were infected intraperitoneally with approximately 5×10$^5$ colony forming units (CFU) *S. aureus* Smith in 7% mucin. One hour later, the animals were given prodrug or Compound 1 intravenously or orally in a dose volume of 0.1 mL/10 g body weight. Each group consisted of eight animals. The prodrugs were prepared immediately before dosing in 40 mM sodium citrate buffer, pH 4. Compound 1 was prepared in 20% HPβCD and warmed until dissolved (IV dosing) or in 0.5% methocel (PO dosing) as a suspension. The mice were observed over a three day period and ED$_{50}$ values were calculated from the resulting % survival curves (Table 2). The term "ND" means not determined. The prodrug ED$_{50}$ values were normalized to the content of Compound 1.

TABLE 2

| | ED$_{50}$ in mg/kg (95% Fiducial Limits) | |
|---|---|---|
| Compound | IV | PO |
| $^a$1 | 3.3 (2.3-5.0) | 3.5 (2.7-4.5) |
| $^a$4a | 3.6 (2.5-5.1) | 4.9 (3.2-8.1) |
| 4b | 4.2 (1.2-7.9) | ND |
| 5 | 4.8 (2.5-8.3) | ND |

TABLE 2-continued

| | ED$_{50}$ in mg/kg (95% Fiducial Limits) | |
|---|---|---|
| Compound | IV | PO |
| 8 | 5.3 (3.2-9.2) | ND |
| $^a$21a | 2.9 (1.9-4.2) | 4.4 (2.6-8.0) |

$^a$The ED$_{50}$ was calculated from the results of two or more experiments conducted on separate days.

Pharmacokinetics of Prodrugs in Animal Models

Animals were weighed and given the prodrug intravenously (mice, rats, or dogs) or orally (mice). The prodrugs were prepared immediately before dosing in 40 mM sodium citrate buffer, pH 4. Compound 1 was prepared in 20% HPβCD and warmed until dissolved (IV dosing), or in 0.5% methocel as a suspension (PO dosing). At 0, 0.08, 0.25, 0.5, 1, 2, 4, 6, 8, and 24 hours, blood was removed (via cardiac puncture in euthanized mice, via orbital sinus puncture in anesthetized rats, or via cephalic vein in conscious dogs) and 200 µL of the plasma supernatant was immediately frozen (−70° C.).

On the day of analysis, the samples were thawed on ice and 100 µL was diluted with 200 µL of acetonitrile. The samples were vortexed and then centrifuged at 3000×g for 5 minutes to pellet the precipitated plasma proteins. The supernatant was analyzed by HPLC, or by LC-MS-MS. A standard curve was constructed by spiking a known quantity of Compound 1 into plasma and then performing serial dilutions in the range of 0.01 to 10 µg/mL. Pharmacokinetic (PK) parameters were calculated by WinNonlin Pro, version 3.1.

The results indicate that, when normalized to the dose, PK parameters for Compounds 4a and 21a were similar to the respective parameters for Compound 1 in all species tested (Table 3a-3d). This indicates that the prodrug form for Compounds 4a and 21a were rapidly converted in vivo to Compound 1, which then exhibited elimination kinetics typically observed for Compound 1. The term "ND" means not determined. The term "NA" means not applicable. The dose of each prodrug was normalized to the Compound 1 dose. The values of the PK parameters for the prodrug form for Compounds 4a and 21a are based on the resulting accumulation and elimination of Compound 1.

TABLE 3a

| | Mouse IV | | |
|---|---|---|---|
| PK Parameters | Cpd 1 | Cpd 4a | Cpd 21a |
| Cmax (ug/ml) | 2.6 | ND | 11 |
| AUC (ug-h/ml) | 1.1 | ND | 28 |
| T$_{1/2}$ (h) | 1 | ND | 1.4 |
| Tmax(h) | 0.13 | ND | 1 |
| MRT (h) | | ND | 2.5 |
| Dose (mg/kg) | 2 | ND | 26 |
| Normalized Dose (mg/kg) | NA | ND | 17.5 |

TABLE 3b

| | Mouse PO | | |
|---|---|---|---|
| PK Parameters | Cpd 1 | Cpd 4a | Cpd 21a |
| Cmax (ug/ml) | 5.9 | 8.3 | 14.3 |
| AUC (ug-h/ml) | 23 | 35 | 44 |
| T$_{1/2}$ (h) | 2.1 | 1.8 | 1.9 |
| Tmax (h) | 1.3 | 2 | 0.5 |

TABLE 3b-continued

| | Mouse PO | | |
|---|---|---|---|
| PK Parameters | Cpd 1 | Cpd 4a | Cpd 21a |
| MRT (h) | | 3.4 | 3.1 |
| Dose (mg/kg) | 10 | 22 | 22 |
| Normalized Dose (mg/kg) | NA | 15 | 15 |

TABLE 3c

| | Rat IV | | |
|---|---|---|---|
| PK Parameters | Cpd 1 | Cpd 4a | Cpd 21a |
| Cmax (ug/ml) | 6.6 | 2.1 | 2.3 |
| AUC (ug-h/ml) | 14 | 7.8 | 9.2 |
| $T_{1/2}$ (h) | 4.5 | 4.3 | 4.1 |
| Tmax (h) | NA | 0.4 | 0.27 |
| MRT (h) | | 4.8 | 4.5 |
| Dose (mg/kg) | 2 | 2 | 2 |
| Normalized Dose (mg/kg) | NA | 1.3 | 1.3 |

TABLE 3d

| | Dog IV | | |
|---|---|---|---|
| PK Parameters | Cpd 1 | Cpd 4a | Cpd 21a |
| Cmax (ug/ml) | 2.3 | 1.1 | 0.9 |
| AUC (ug-h/ml) | 2.8 | 2.4 | 4.2 |
| $T_{1/2}$ (h) | 1.8 | 3.1 | 3.3 |
| Tmax (h) | NA | 1.0 | 0.58 |
| MRT (h) | | 4.2 | 4.9 |
| Dose (mg/kg) | 1 | 2 | 2 |
| Normalized Dose (mg/kg) | NA | 1.3 | 1.3 |

The above description is intended for illustrative purposes only, and does not limit the scope of the invention, which is defined in the following claims.

We claim:

1. A compound having the Formula (II):

wherein:
$R^1$ is hydrogen or lower alkyl;
$R^2$ is selected from the group consisting of wherein, n is 0, 1, 2, 3 or 4;
X is selected from the group consisting of amino optionally substituted by one or two lower alkyl; heterocyclyl optionally substituted by one or more lower alkyl; and —O—PO$_3$H$_2$ or an alkyl ester thereof;
Y is selected from the group consisting of —CH$_2$O—PO$_3$H$_2$ or an alkyl ester thereof, and —O—PO$_3$H$_2$ or an alkyl ester thereof;
$R^3$ is hydrogen or lower alkyl; or
a pharmaceutically acceptable salt thereof.

2. The compound of claim 1, wherein
$R^1$ is hydrogen or lower alkyl;
$R^2$ is selected from the group consisting of wherein n is 1;
X is selected from the group consisting of amino optionally substituted by one or two lower alkyl; and, heterocyclyl, optionally substituted by one or more lower alkyl;
$R^3$ is lower alkyl; or
a pharmaceutically acceptable salt thereof.

3. The compound of claim 1, wherein
$R^1$ is hydrogen or methyl;
$R^2$ is selected from the group consisting of wherein n is 1;
X is selected from the group consisting of amino optionally substituted by one or two methyl; and, pyrrolidinyl, piperazinyl or morpholinyl, optionally substituted on pyrrolidinyl or piperazinyl by one methyl;
$R^3$ is ethyl; or
a pharmaceutically acceptable salt thereof.

4. The compound of claim 3, wherein X is selected from the group consisting of amino optionally substituted by one or two methyl; and, piperazinyl optionally substituted by one methyl.

5. A compound selected from the group consisting of:
piperazin-1-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
Piperazin-1-yl-acetic acid 1-(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-ethyl ester,
Dimethylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
Morpholin-4-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
1-Methyl-pyrrolidine-2-carboxylic acid (acetyl-{(R)-3-[3-fluoro-4-(2-methyl-2,6-dihydro-4H-pyrrolo[3,4-c]

pyrazol-5-yl)-phenyl]-2-oxo-oxazolidin-5-ylmethyl}-carbamoyloxy)-methyl ester,
(4-Methyl-piperazin-1-yl)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
(tert-Butoxycarbonyl-methyl-amino)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
Methylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
(S)-Pyrrolidine-1,2-dicarboxylic acid 2-[(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl]ester 1-tert-butyl ester,
(S)-Pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
4-(Bis-benzyloxy-phosphoryloxymethyl)-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
4-Phosphonooxymethyl-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
4-(Bis-benzyloxy-phosphoryloxy)-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
4-Phosphonooxy-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid di-tert-butoxy-phosphoryloxymethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(di-tert-butoxy-phosphoryloxy)-ethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid phosphonooxymethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-phosphonooxy-ethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid benzyloxy-ethoxy-phosphoryloxymethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(benzyloxy-ethoxy-phosphoryloxy)-ethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid ethoxy-hydroxy-phosphoryloxymethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(ethoxy-hydroxy-phosphoryloxy)-ethyl ester,
(Di-tert-butoxy-phosphoryloxy)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, and
Phosphonooxy-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester.

6. The compound of claim 5, wherein the compound is selected from the group consisting of:
Piperazin-1-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
Piperazin-1-yl-acetic acid 1-(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-ethyl ester,
Dimethylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
Morpholin-4-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
1-Methyl-pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
(4-Methyl-piperazin-1-yl)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
Methylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
(S)-Pyrrolidine-2-carboxylic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
4-Phosphonooxymethyl-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
4-Phosphonooxy-benzoic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid phosphonooxymethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-phosphonooxy-ethyl ester,
Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid ethoxy-hydroxy-phosphoryloxymethyl ester, Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid 1-(ethoxy-hydroxy-phosphoryloxy)-ethyl ester, and Phosphonooxy-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester.

7. The compound of claim 6, wherein the compound is selected from the group consisting of:

Piperazin-1-yl-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, Piperazin-1-yl-acetic acid 1-(acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-ethyl ester, Dimethylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, (4-Methyl-piperazin-1-yl)-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, Methylamino-acetic acid (acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamoyloxy)-methyl ester, and Acetyl-{(R)-3-[3-fluoro-4-(2-methyl-2,6-dihydro-4H-pyrrolo[3,4-c]pyrazol-5-yl)-phenyl]-2-oxo-oxazolidin-5-ylmethyl}-carbamic acid ethoxy-hydroxy-phosphoryloxymethyl ester.

8. A pharmaceutical formulation comprising a compound of claim 1 as an active pharmaceutical ingredient, and one or more pharmaceutically acceptable excipients.

* * * * *